US010512753B1

(12) United States Patent
Nguyen

(10) Patent No.: US 10,512,753 B1
(45) Date of Patent: Dec. 24, 2019

(54) COMPOSITE CATHETER SHAFTS AND METHODS AND APPARATUS FOR MAKING THE SAME

(71) Applicant: John Nguyen, Irvine, CA (US)

(72) Inventor: John Nguyen, Irvine, CA (US)

( * ) Notice: Subject to any disclaimer, the term of this patent is extended or adjusted under 35 U.S.C. 154(b) by 0 days.

(21) Appl. No.: 16/213,872

(22) Filed: Dec. 7, 2018

(51) Int. Cl.
*A61M 25/00* (2006.01)

(52) U.S. Cl.
CPC .... *A61M 25/0053* (2013.01); *A61M 25/0045* (2013.01); *A61M 25/0054* (2013.01); *A61M 2025/0063* (2013.01)

(58) Field of Classification Search
CPC ............ A61M 25/005; A61M 25/0053; A61M 25/0054; A61M 2025/0063; A61M 25/0009; A61M 25/0012; A61M 25/0052; A61M 25/0144
See application file for complete search history.

(56) References Cited

U.S. PATENT DOCUMENTS

| | | | |
|---|---|---|---|
| 5,484,424 A * | 1/1996 | Cottenceau | A61F 2/01 604/525 |
| 5,554,139 A | 9/1996 | Okajima | |
| 5,662,622 A | 9/1997 | Gore et al. | |
| 5,795,341 A | 8/1998 | Samson | |
| 5,879,499 A | 3/1999 | Corvi | |
| 5,891,112 A | 4/1999 | Samson | |
| 5,947,940 A | 9/1999 | Beisel | |
| 5,951,539 A | 9/1999 | Nita et al. | |
| 5,997,487 A * | 12/1999 | Kolehmainen | A61M 25/0009 600/585 |
| 6,152,912 A | 11/2000 | Jansen et al. | |
| 6,165,163 A | 12/2000 | Chien et al. | |
| 6,186,978 B1 | 2/2001 | Samson et al. | |
| 6,451,005 B1 | 9/2002 | Saitou et al. | |
| 6,508,804 B2 * | 1/2003 | Sarge | A61M 25/005 604/524 |
| 6,511,462 B1 | 1/2003 | Itou et al. | |
| 6,589,227 B2 | 7/2003 | Sønderskov | |
| 6,652,508 B2 | 11/2003 | Griffin et al. | |
| 6,896,671 B2 | 5/2005 | Vitullo et al. | |
| 7,115,183 B2 | 10/2006 | Larson et al. | |
| 7,674,252 B2 | 3/2010 | De Vaux | |
| 7,763,012 B2 | 7/2010 | Petrick et al. | |
| 7,771,411 B2 | 8/2010 | Smith et al. | |
| 7,815,627 B2 | 10/2010 | Von Oepen et al. | |
| 7,833,175 B2 | 11/2010 | Parins | |
| 7,905,877 B1 | 3/2011 | Jimenez et al. | |
| 8,235,968 B2 | 8/2012 | Tremaglio | |

(Continued)

*Primary Examiner* — Quynh-Nhu H. Vu
(74) *Attorney, Agent, or Firm* — Blair Walker IP Services, LLC

(57) ABSTRACT

A medical device includes an elongate shaft including a multifilar coil comprising a first strand and a second strand wound in the same winding direction, the multifilar coil comprising a first section having a first end and a second end wherein the first strand and the second strand are wound with identical pitch patterns between the first end and the second end of the first section, the multifilar coil further comprising a second section having a first end and a second end, wherein the first strand and the second strand are wound with different pitch patterns from each other between the first end and second end of the second section, and a polymeric tubular member coextending with the multifilar coil.

23 Claims, 12 Drawing Sheets

(56) References Cited

U.S. PATENT DOCUMENTS

| | | |
|---|---|---|
| 8,246,536 B2 | 8/2012 | Ochi et al. |
| 8,246,574 B2 | 8/2012 | Jacobs et al. |
| 8,303,569 B2 | 11/2012 | Lobbins et al. |
| 8,317,772 B2 | 11/2012 | Jansen et al. |
| 8,403,912 B2 | 3/2013 | McFerran et al. |
| 8,534,176 B2 | 9/2013 | Giszter et al. |
| 8,535,293 B2 | 9/2013 | Faherty et al. |
| 8,540,695 B2 | 9/2013 | Shimogami et al. |
| 8,636,716 B2 | 1/2014 | Griffin et al. |
| 8,833,224 B2 | 9/2014 | Thompson et al. |
| 8,951,240 B2 | 2/2015 | Saito et al. |
| 9,023,011 B2 | 5/2015 | Griffin et al. |
| 9,550,042 B2 | 1/2017 | Tanioka |
| 9,631,303 B2 | 4/2017 | Marchand et al. |
| 9,656,042 B2 | 5/2017 | Tagaki et al. |
| 9,844,643 B2 * | 12/2017 | Beasley ................. A61N 1/056 |
| 2002/0156460 A1 | 10/2002 | Ye et al. |
| 2003/0236505 A1 | 12/2003 | Bonadio et al. |
| 2016/0346503 A1 | 12/2016 | Jackson et al. |
| 2017/0072163 A1 | 3/2017 | Lim et al. |
| 2017/0072165 A1 | 3/2017 | Lim et al. |
| 2017/0182290 A1 * | 6/2017 | Stern ................. A61M 25/0053 |
| 2017/0368303 A1 | 12/2017 | Nakayama et al. |
| 2018/0104440 A1 | 4/2018 | Hanaoka |
| 2018/0140808 A1 | 4/2018 | Kubo |

* cited by examiner

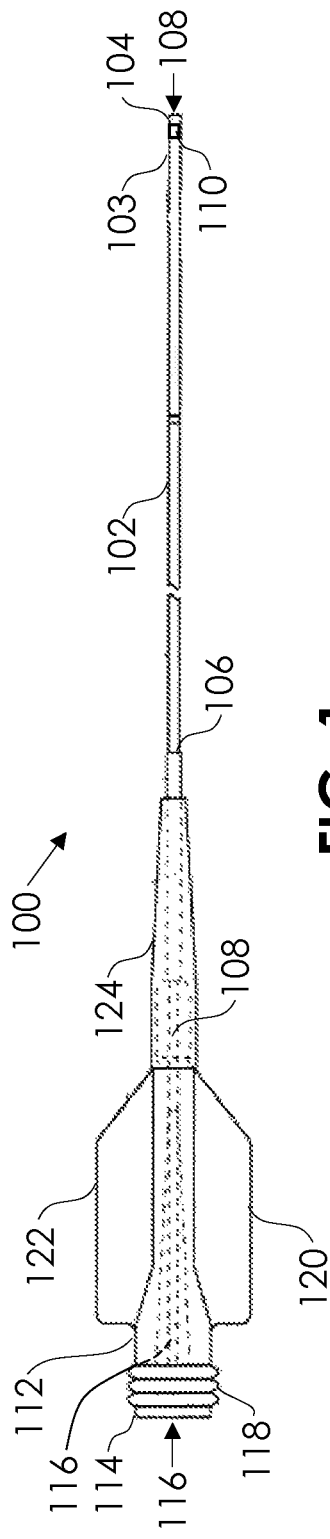
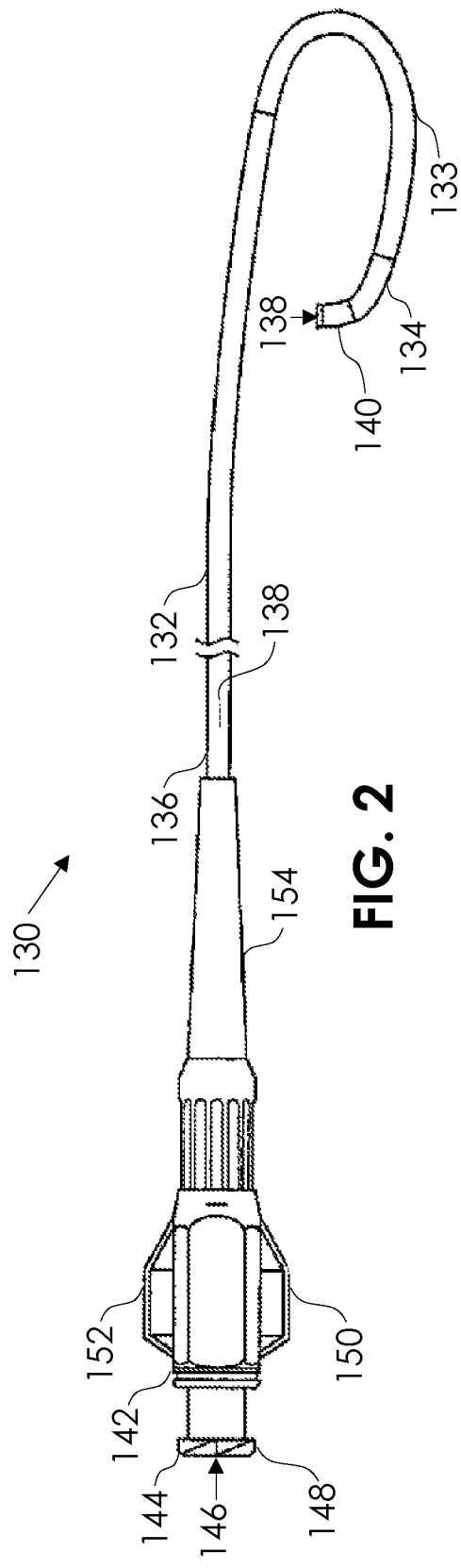
FIG. 1
FIG. 2

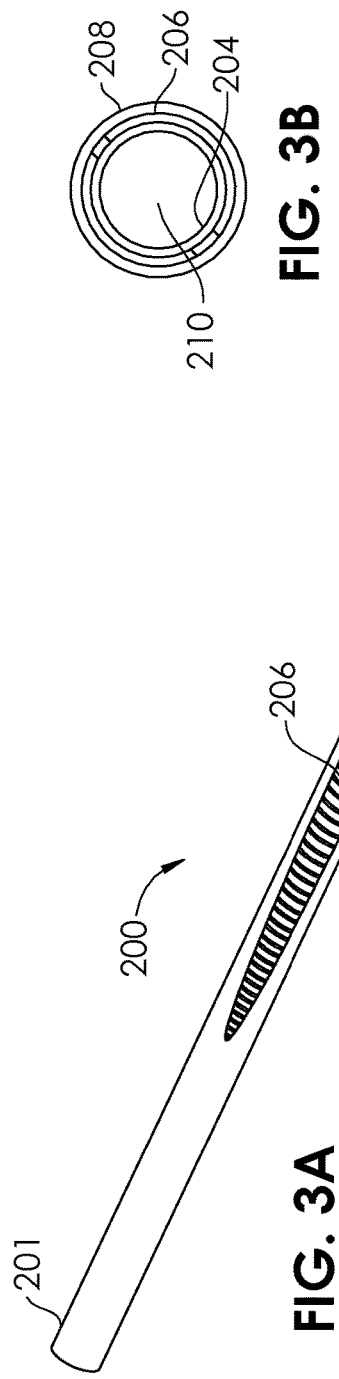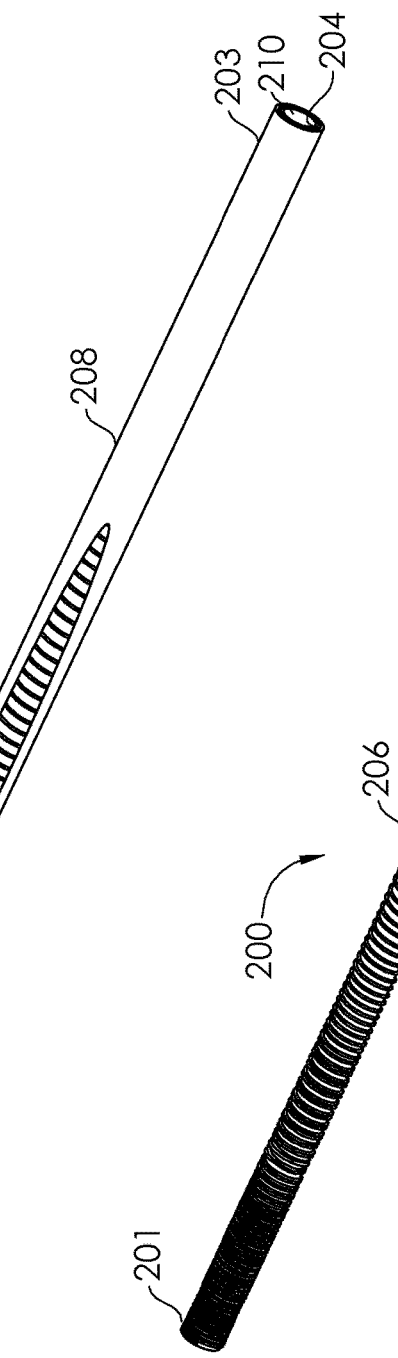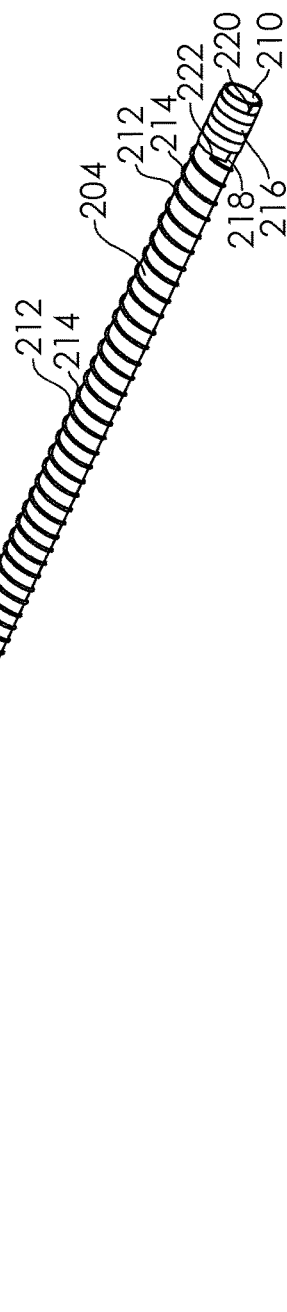

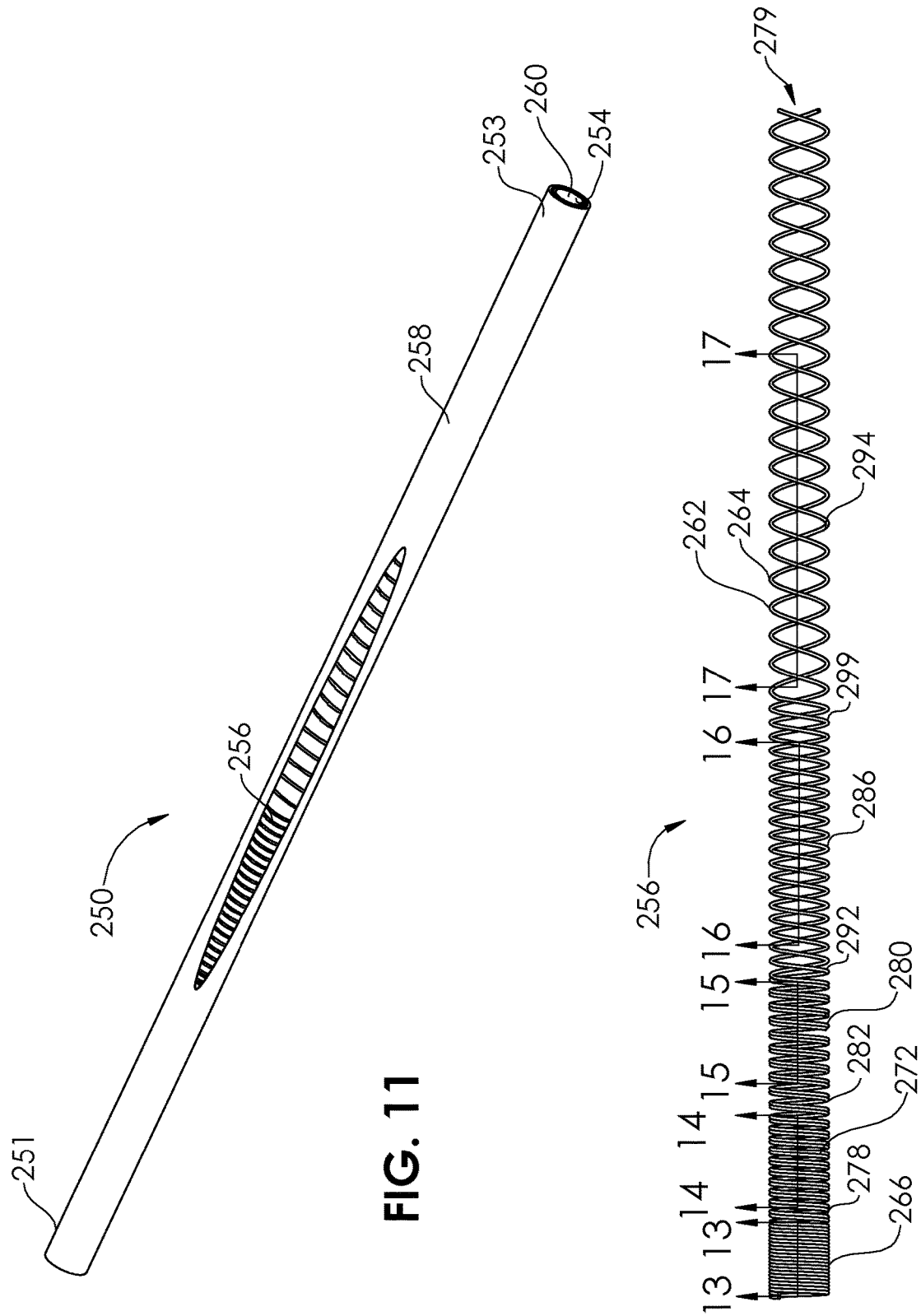

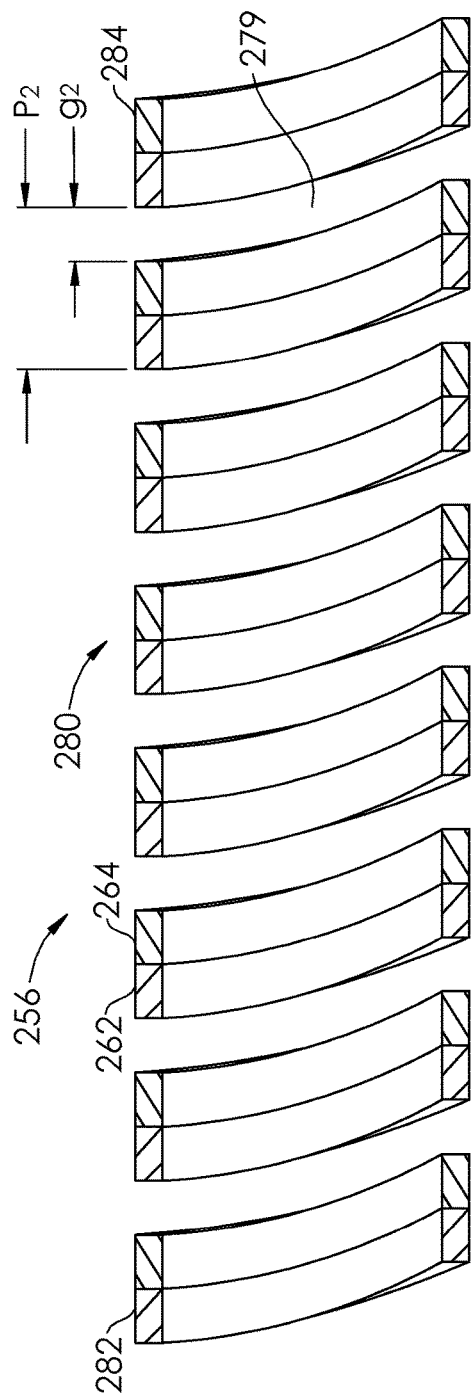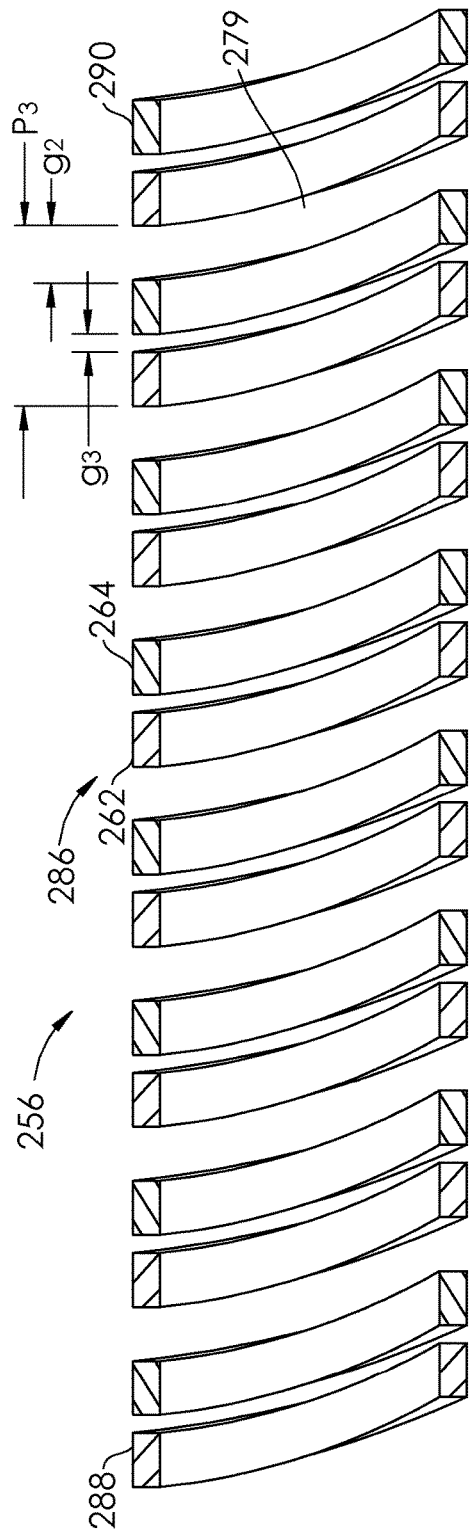
FIG. 15
FIG. 16

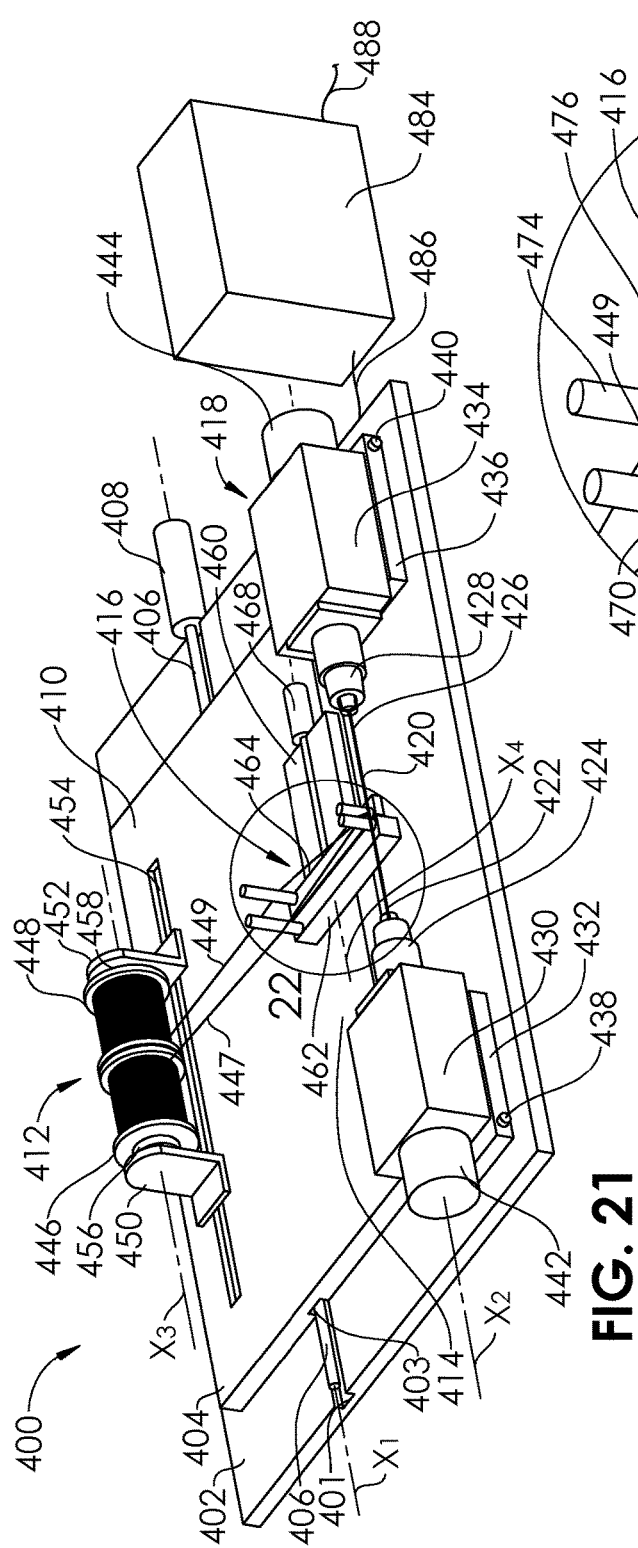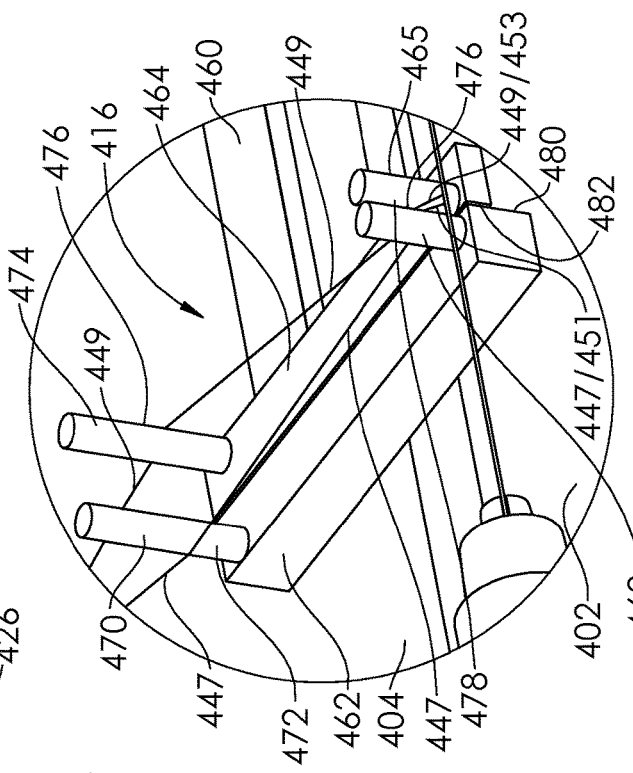

COMPOSITE CATHETER SHAFTS AND METHODS AND APPARATUS FOR MAKING THE SAME

FIELD OF THE INVENTION

The field of the invention generally relates to elongate medical devices such as catheters, and particularly to composite shafts used in these devices.

BACKGROUND

Elongate medical devices are used to access interior portions of patients' bodies. Oftentimes, the pathway to the site of interest within the body can be tortuous, small in size, obstructive, significantly angulated, or a combination of these factors. The medical devices, including catheter, often have elongate shafts that aid the tracking or accessing of the site or sites of interest. Medical device shafts are commonly designed with the purpose of achieving the desired combination of flexibility, profile, trackability, pushability, tensile strength, lubricity. However, the shafts oftentimes have other requirements, the fulfillment of which can compromise the previously described attributes, such as the need to place other medical devices within them, to transfer fluids (injection and aspiration) and to envelop of otherwise carry elongate operative components (electrical wires, optical fibers, etc.).

SUMMARY OF THE INVENTION

In a first embodiment of the present disclosure, a medical device includes an elongate shaft including a first coil having a proximal end and a distal end, the first coil wound in a first direction, a second coil having a proximal end and a distal end, the second coil wound in the first direction, the second coil and first coil arranged together such that a wind of the first coil is longitudinally successive to a wind of the second coil, wherein at a first longitudinal location on the shaft, the first coil has an outer diameter, an inner diameter, and a first pitch and at a second longitudinal location on the shaft the first coil has an outer diameter, an inner diameter, and a second pitch, the second pitch of the first coil larger than the first pitch of the first coil, and wherein at the first longitudinal location on the shaft, the second coil has an outer diameter, an inner diameter, and a first pitch and at the second location on the shaft, the second coil has an outer diameter, an inner diameter, and a second pitch, the second pitch of the second coil larger than the first pitch of the second coil, wherein the outer diameter of the first coil at the first longitudinal location is greater than the inner diameter of the second coil at the first longitudinal location and the inner diameter of the first coil at the first longitudinal location is less than the outer diameter of the second coil at the first longitudinal location, and wherein the first pitch of the first coil at the first longitudinal location and the first pitch of the second coil at the first longitudinal location are substantially the same, and wherein the second pitch of the first coil at the second longitudinal location and the second pitch of the second coil at the second longitudinal location are different from each other, and a polymeric tubular member coextending with and at least partially coupled to at least one of the first coil or second coil.

In another embodiment of the present disclosure, a medical device includes an elongate shaft including a multifilar coil comprising a first strand and a second strand wound in the same winding direction, the multifilar coil comprising a first section having a first end and a second end wherein the first strand and the second strand are wound with identical pitch patterns between the first end and the second end of the first section, the multifilar coil further comprising a second section having a first end and a second end, wherein the first strand and the second strand are wound with different pitch patterns from each other between the first end and second end of the second section, and a polymeric tubular member coextending with the multifilar coil.

In still another embodiment of the present disclosure, a multifilar coil includes a first strand and a second strand wound in the same winding direction, the multifilar coil comprising a first section having a first end and a second end wherein the first strand and the second strand have similar pitch patterns between the first end and the second end of the first section, the multifilar coil further comprising a second section having a first end and a second end, wherein the first strand and the second strand have different pitch patterns from each other between the first end and second end of the second section.

In yet another embodiment of the present disclosure, an elongate shaft includes a multifilar coil including a first strand and a second strand wound in the same winding direction, the multifilar coil comprising a first section having a first end and a second end wherein the first strand and the second strand have similar pitch patterns between the first end and the second end of the first section, the multifilar coil further comprising a second section having a first end and a second end, wherein the first strand and the second strand have different pitch patterns from each other between the first end and second end of the second section, and a polymeric tubular member coextending with the multifilar coil.

In still another embodiment of the present disclosure, a method of making a multifilar coil includes securing a first portion of a first strand and a first portion of a second strand to a mandrel, causing relative rotation and relative longitudinal displacement to simultaneously occur between a first unsecured portion of the first strand and the mandrel and between a first unsecured portion of the second strand and the mandrel, such that the first unsecured portion of the first strand and the first unsecured portion of the second strand are each caused to form a first helical shape, the first helical shape of the first strand in the same winding direction as the first helical shape of the second strand, the first helical shape of the first strand having a pitch pattern that is similar to the pitch pattern of the first helical shape of the second strand, and further causing relative rotation and relative longitudinal displacement to simultaneously occur between a second unsecured portion of the first strand and the mandrel and between a second unsecured portion of the second strand and the mandrel while causing a longitudinal distance between the second unsecured portion of the first strand and the second unsecured portion of the second strand to change, such that the second unsecured portion of the first strand is caused to form a second helical shape and the second unsecured portion of the second strand is caused to form a third helical shape helical shape, the second helical shape of the first strand in the same winding direction as the third helical shape of the second strand, the second helical shape of the first strand having a pitch pattern that is different from a pitch pattern of the third helical shape of the second strand.

In yet another embodiment of the present disclosure, a medical device includes an elongate shaft including a multifilar coil comprising a first strand and a second strand wound in the same winding direction, the multifilar coil comprising a first close-wound portion having a first end and a second end wherein the first strand and the second strand have substantially no longitudinal gap between each other between the first end and second end of the first close-wound portion, the multifilar coil further comprising a first open-wound portion having a first end and a second end wherein the first strand and the second strand have substantially no longitudinal gap between each other between the first end and second end of the first open-wound portion, the multifilar coil further comprising a second open-wound portion having a first end and a second end wherein the first strand and the second strand have a longitudinal gap between the first end and second end of the second open-wound portion, and a polymeric tubular member coextending with the multifilar coil.

In still another embodiment of the present disclosure, a mechanism for making a multifilar coil includes a mandrel having a longitudinal axis and configured for securing a first strand and a second strand thereto, a holder configured for carrying an unsecured portion of the first strand and an unsecured portion of the second strand, the holder and the mandrel configured for relative rotation and longitudinal displacement with respect to each other, a first engagement member disposed on the holder and configured to engage the unsecured portion of the first strand, and a second engagement member disposed on the holder and configured to engage the unsecured portion of the second strand, the first engagement member and second engagement member configured to change their relative longitudinal separation with respect to each other while the relative rotational and longitudinal orientation between the mandrel and the holder is caused to change.

In yet another embodiment of the present disclosure, a method of making a multifilar coil includes securing a first portion of a first strand and a first portion of a second strand to a mandrel, causing relative rotation and relative longitudinal displacement to simultaneously occur between an unsecured portion of the first strand and the mandrel and between an unsecured portion of the second strand and the mandrel, and changing the relative longitudinal distance between the unsecured portion of the first strand and the unsecured portion of the second strand.

BRIEF DESCRIPTION OF THE DRAWINGS

FIG. 1 is a plan view of a microcatheter, according to an embodiment of the present disclosure.

FIG. 2 is a plan view of a guiding catheter, according to an embodiment of the present disclosure.

FIG. 3A is a perspective partially cut-away view of a composite shaft according to an embodiment of the present disclosure.

FIG. 3B is a cross-sectional view of the composite shaft of FIG. 3A.

FIG. 4 is a perspective view of the composite shaft of FIG. 4 with an outer layer removed.

FIG. 11 is a perspective partially cut-away view of a composite shaft according to an embodiment of the present disclosure.

FIG. 12 is a plan view of a multifilar coil of the composite shaft of FIG. 11.
FIG. 15 is as sectional view taken from lines 15-15 of FIG. 12.
FIG. 16 is as sectional view taken from lines 16-16 of FIG. 12.

FIG. 21 is a perspective view of a machine for winding a composite coil, according to an embodiment of the present disclosure.

FIG. 22 is a detail view of circle 22 of FIG. 21.

DETAILED DESCRIPTION

Figure 5:
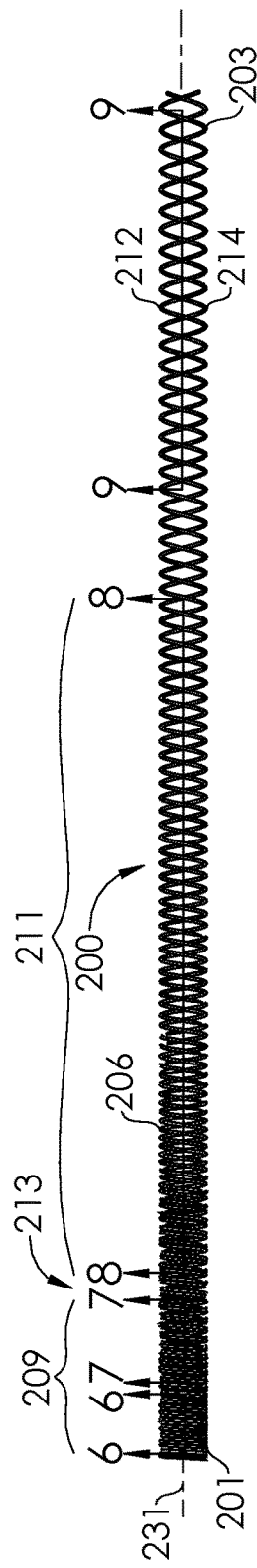
FIG. 5 is a plan view of a multifilar coil of the composite shaft of FIG. 3A.

FIG. 1 illustrates a microcatheter 100 configured to provide access to vasculature of a patient. The microcatheter 100 comprises a tubular shaft 102 having a distal end 104 and a proximal end 106, and a lumen 108 extending between the distal end 104 and the proximal end 106. The microcatheter 100 may include a radiopaque marker 110 at its distal end, which may comprise a platinum band. The radiopaque marker 110 is configured to be visible on x-ray or fluoroscopy by a user during an interventional procedure, when the microcatheter 100 is being tracked through the blood vessels of the patient. A hub 112 is coupled to the proximal end 106 of the tubular shaft 102, and comprises a female luer connector 114 having an internal luer taper 116, and one or more external male threads 118. The internal luer taper 116 and the external male threads 118 are configured for attaching a syringe, or any type of male luer connector thereto. This may include the male luer of a y-connector or other type of connector. The hub 112 includes wings 120, 122, which are configured to allow a torque to be placed on the hub 112 the a male luer is being attached to or detached from the hub 112. The wings 120, 122 may be used to apply a torque to at least partially rotate the microcatheter 100, for example, to orient a curve formed in the distal portion 103, so that access is better provided into a blood vessel (artery, vein) branch, or into a vascular feature or defect, such as an aneurysm, a arterio-venous malformation (AVM), a left anterior appendage (LAA), a patent foramen ovale (PFO), or an atrial septal defect (ASD). The wings 120, 122 may even be used to apply a torque to attempt to dislodge the guiding catheter 130 from a situation in which it has become stuck. A strain relief 124 comprises a tapered tubular element comprising a soft, flexible material (e.g., silicone, thermoplastic elastomer, or other elastomer) that protects against kinking of the tubular shaft 102 at its proximal end 106. The strain relief 124 extends between the hub 112 and the proximal end 106 of the tubular shaft 102 and may at least partially cover a portion of the hub 112 and a portion of the tubular shaft 102. In some embodiments, the strain relief 124 may include a flat wire coil or a laser machined tube or hypo tube having a helical cut. The flat wire coil or helically-cut tube or hypo tube may comprise a metal or a stiff polymeric material, and may be carried on the proximal end 106 of the tubular shaft 102, and covered with a protective tube comprising a soft, flexible material (e.g., silicone, thermoplastic elastomer, or other elastomer).

The microcatheter 100 may be tracked into blood vessels (arteries or veins) in the majority of the locations in the body of a patient, including, but not limited to peripheral arteries, coronary arteries, renal arteries, a pulmonary artery, cerebral arteries, and internal or external carotid arteries. In some cases, the microcatheter 100 is configured to be placed down the lumen 146 of the guiding catheter 130. A guidewire may be inserted down the lumen 146 of the guiding catheter 130 to guide the placement of the guiding catheter 130, or to perform other functions, such as the tracking of other catheters, including potentially the microcatheter 100. The tubular shaft 102 may comprise one or more polymeric materials, and can incorporate any of the embodiments of the composite catheter shafts disclosed herein.

FIG. 2 illustrates a guiding catheter 130 configured to provide access to vasculature of a patient. The guiding catheter 130 comprises a tubular shaft 132 having a distal end 134 and a proximal end 136, and a lumen 138 extending between the distal end 134 and the proximal end 136. The guiding catheter 130 may include a radiopaque marker 140 at its distal end, which may comprise a platinum band. The radiopaque marker 140 is configured to be visible on x-ray or fluoroscopy by a user during an interventional procedure, when the microcatheter 100 is being tracked through the blood vessels of the patient. A hub 142 is coupled to the proximal end 146 of the tubular shaft 142, and comprises a female luer connector 144 having an internal luer taper 146, and one or more external male threads 148. The internal luer taper 146 and the external male threads 148 are configured for attaching a syringe, or any type of male luer connector thereto. This may include the male luer of a y-connector or other type of connector. The hub 142 includes wings 150, 152, which are configured to allow a torque to be placed on the hub 142 the a male luer is being attached to or detached from the hub 142. The wings 150, 152 may also be used to apply a torque to rotate the guiding catheter 130, for example, to orient the distal curve 133 in a desired position. A strain relief 154 comprises a tapered tubular element comprising a soft, flexible material (e.g., silicone, thermoplastic elastomer, or other elastomer) that protects against kinking of the tubular shaft 132 at its proximal end 136. The strain relief 154 extends between the hub 142 and the proximal end 136 of the tubular shaft 132 and may at least partially cover a portion of the hub 142 and a portion of the tubular shaft 132. In some embodiments, the strain relief 124 may include a flat wire coil or a laser machined tube or hypo tube having a helical cut. The flat wire coil or helically-cut tube or hypo tube may comprise a metal or a stiff polymeric material, and may be carried on the proximal end 106 of the tubular shaft 102, and covered with a protective tube comprising a soft, flexible material (e.g., silicone, thermoplastic elastomer, or other elastomer). The guiding catheter 130 may be tracked into blood vessels (arteries or veins) in the majority of the locations in the body of a patient, including, but not limited to peripheral arteries, coronary arteries, renal arteries, a pulmonary artery, cerebral arteries, and internal or external carotid arteries. A guidewire may be inserted down the lumen 116 of the microcatheter 100 to guide the placement of the microcatheter 100. The tubular shaft 132 may comprise one or more polymeric materials, and can incorporate any of the embodiments of the composite catheter shafts disclosed herein.

The guiding catheter 130 need not have a distal curve 133. Nor must the distal end 134 be configured for cannulating a vessel branch or vascular feature. In other embodiments, the guiding catheter 130 may comprise a straight shaft that is configured to apply backup support to other catheters that are placed through its lumen 138. The guiding catheter 130 may simply comprise a long sheath, often referred to as a guide sheath. In some embodiments, a guide sheath may be configured for placing another, smaller diameter guiding catheter through its lumen 138. For example, a 6 French diameter guiding catheter may be placed through an 8 French diameter guide sheath. The guide sheath may be configured for direct percutaneous introduction into a patient, used in conjunction with a dilator and a guidewire, using the Seldinger technique.

FIGS. 3A and 3B illustrate a composite shaft 200 which may be configured to serve as the tubular shaft 102 of FIG. 1, the tubular shaft 132 of FIG. 2, or another type of medical device shaft. The composite shaft 200 has a proximal end 201 and a distal end 203, and comprises a tubular inner polymeric layer 204, a coil layer 206, and a tubular outer polymeric layer 208. A lumen 210 passes through the composite shaft 200 and has a circular cross-section. In other embodiments, the lumen 210 may have a non-circular cross-section. I still other embodiments, the lumen 210 may comprise two or more lumens. The inner polymeric layer 204 (often referred to in the catheter art as a "liner") may comprise an extruded tube, and may comprise a number of materials, including lubricious or low-friction materials, such as PTFE, ETFE, or FEP. The inner polymeric layer 204 may also comprise common catheter materials such as polyamide, polyimide, or thermoplastic elastomers, such as polyether block amide. A low friction material may be desirable for constructing the inner polymeric layer 204 if, for example, the lumen 210 is to be used for the passage of a guidewire or of another medical shaft or elongate medical device, such as an embolic coil. The low-friction materials often display "non-stick" characteristics because of their relatively low surface energy. Thus, these materials may be used for constructing the inner polymeric layer 204 when applications involve injecting materials through the lumen 210 wherein good release of the material is desired. These injected materials may include embolic materials such as cyanoacrylate (e.g., N-butyl-2 cyanoacrylate), gelatin foam, polyvinyl alcohol, ethylene vinyl alcohol copolymer, tris-acryl gelatin microspheres, or calcium alginate gel. In other embodiments, a lubricious material may be injected through the lumen 210 to create a low-friction coating. In some embodiments, the material may comprise Baymedix® CL 100 manufactured by Bayer Material Science, LLC of Pittsburgh, Pa., USA. Baymedix is a registered trademark of Covestro Deutschland AG of Leverkusen, Federal Republic of Germany.

The coil layer 206 comprises a multifilar coil which includes two or more different spiral coils. The coil layer 206 is illustrated in FIG. 4 with the outer polymeric layer 208 (often referred to in the catheter art as a "jacket") removed from view. The coil layer 206 includes a first spiral-wound filament or strand 212 and a second spiral-wound filament or strand 214. In some embodiments, both the first spiral-wound strand 212 and the second spiral-wound strand 214 comprise a metallic material. In other embodiments, both the first spiral-wound strand 212 and the second spiral-wound strand 214 comprise a liquid crystal polymer. In other embodiments, one of the first spiral-wound strand 212 or the second spiral-wound strand 214 comprises a metallic material and the other of the first spiral-wound strand 212 and the second spiral-wound strand 214 comprises a liquid crystal polymer.

In some embodiments, both the first spiral-wound strand 212 and the second spiral-wound strand 214 comprise a round wire. In other embodiments, both the first spiral-wound strand 212 and the second spiral-wound strand 214 comprise a non-round wire, for example, flat wire. In other embodiments, one of the first spiral-wound strand 212 or the second spiral-wound strand 214 comprises a round wire and the other of the first spiral-wound strand 212 and the second spiral-wound strand 214 comprises a non-round wire. In some embodiments, both the first spiral-wound strand 212 and the second spiral-wound strand 214 comprise a highly radiopaque material, such as platinum. In other embodiments, both the first spiral-wound strand 212 and the second spiral-wound strand 214 comprise a high strength material, such as stainless steel. In other embodiments, one of the first spiral-wound strand 212 or the second spiral-wound strand 214 comprises a radiopaque material, such as platinum, and the other of the first spiral-wound strand 212 and the second spiral-wound strand 214 comprises a high strength material, such as stainless steel. The first spiral-wound strand 212 and/or the second spiral-wound strand 214 may comprise platinum, or a platinum alloy, such as 92% platinum.8% tungsten. In other embodiments, the spiral-wound strand 212 and/or the second spiral-wound strand 214 may comprise a drawn filled tube (DFT®), which may comprise a radiopaque core, such as a platinum core, surrounded by a cylindrical jacket of a high strength material, such as stainless steel, or nickel-titanium alloy. The drawn filled tube is a composite wire that has good mechanical properties, with many similarities to high strength materials, but also has a degree of radiopacity. Thus, by any of the combinations described, the mechanical characteristics as well as the radiopacity (or lack thereof) of the spiral-wound strand 212 or the second spiral-wound strand 214 can be tailored. This may be important because cases scenarios exist in which x-ray or fluoroscopic visualization of at least some portion of the composite shaft 200 is desired, but wherein too much radiopacity may obscure or mask certain anatomical features or other radiopaque devices within the region of interest in the patient. Drawn filled tube (DFT®) is a registered trademark of, and may be obtained from Fort Wayne Metals Research Products Corp. of Fort Wayne, Ind., USA.

In some embodiments, both the first spiral-wound strand 212 and the second spiral-wound strand 214 have the same (wound) outer diameter. In other embodiments, the first spiral-wound strand 212 has a different (wound) outer diameter from the second spiral-wound strand 214. In some embodiments, both the first spiral-wound strand 212 and the second spiral-wound strand 214 have the same (wound) inner diameter. In other embodiments, the first spiral-wound strand 212 has a different (wound) inner diameter from the second spiral-wound strand 214. In some embodiments, both the first spiral-wound strand 212 and the second spiral-wound strand 214 are flat wire and have the same maximum transverse dimension (of the flat strand cross-section). In other embodiments, both the first spiral-wound strand 212 and the second spiral-wound strand 214 are flat wire, but have different maximum transverse dimensions (of the flat strand cross-section). In some embodiments, both the first spiral-wound strand 212 and the second spiral-wound strand 214 are round wire and have the same maximum diameter (of the circular strand cross-section). In other embodiments, both the first spiral-wound strand 212 and the second spiral-wound strand 214 are round wire, but have different diameters (of the circular strand cross-section). The diameter or maximum transverse dimension of the wire in the first spiral-wound strand 212 or the second spiral-wound strand 214 may be between about 0.0005 inch and about 0.015 inch, or between about 0.001 inch and about 0.005 inch.

The first spiral-wound strand 212 and the second spiral-wound strand 214 are wound in the same spiral direction (e.g., left-hand or right-hand) as each other, but are constructed with pitch patterns (winding patterns) that differ from each other. The term "pitch pattern" is used herein in a broad sense to describe the how the pitch (distance between successive winds) varies along the length of each spiral-wound strand. The pitch pattern may be completely realized during the winding process, or the pitch pattern may be at least partially created by subsequently stretching or compressing a portion or all of the spiral-wound strand, after it has been initially wound. The coil layer 206 may be treated after being wound. For example, if either of the first spiral-wound strand 212 or the second spiral-wound strand 214 comprises a nickel-titanium alloy or other shape memory material, the wound pattern may be heat set at an elevated temperature, while restrained, in order to impart memory into the wound shape. If either of the first spiral-wound strand 212 of the second spiral-wound strand 214 comprises a heat-treatable material, such as stainless steel, it may be heat treated by exposing it to an elevated temperature.

The first spiral-wound strand 212 and second spiral-wound strand 214 coaxially commingle with each other to embody the multifilar coil of the coil layer 206. The first spiral-wound strand 212 and the second spiral-wound strand 214 are wound, manually, or with a winding machine, together over the inner polymeric layer 204. A mandrel may be inserted down the lumen 210 of the inner polymeric layer 204 to stiffen and support the inner polymeric layer 204 during winding. Alternatively, the first spiral-wound strand 212 may be wound in its entirety over the inner polymeric layer 204, and subsequently, the second spiral-wound strand 214 may be wound in its entirety over the inner polymeric layer 204. In other embodiments, the first spiral-wound strand 212 and the second spiral-wound strand 214 may be wound over a mandrel, the mandrel subsequently removed, and the inner polymeric layer 204 inserted through the joint inner lumen of the first spiral-wound strand 212 and the second spiral-wound strand 214. In still other embodiments, the first spiral-wound strand 212 may be wound over and mandrel, the second spiral-wound strand 214 may be wound separately over a mandrel, the first spiral-wound strand 212 and the second spiral-wound strand 214 may each have their mandrels removed and the first spiral-wound strand 212 and the second spiral-wound strand 214 may be manipulated so that they are fit together. Subsequently, the inner polymeric layer 204 is inserted through the joint inner lumen of the first spiral-wound strand 212 and the second spiral-wound strand 214. In some embodiments, if the composite shaft 200 does not have an inner lumen, it may be sufficiently stiff enough such that a mandrel is not required.

Each successive wind of the coil layer 206 comprises a different alternating strand (first spiral-wound strand 212, second spiral-wound strand 214, first spiral-wound strand 212, second spiral-wound strand 214, etc.). Though the embodiment of FIGS. 3A-4 comprises a bifilar coil, in alternative embodiments that are trifilar, quadrifilar, or more, the alternating strands would also be a feature. For example, in a trifilar coil, the strands would alternate as follows: first spiral-wound strand, second spiral-wound strand, third spiral-wound strand, first spiral-wound strand, second spiral-wound strand, third spiral-wound strand, etc. FIG. 4 also illustrates a distal radiopaque marker 216. The distal radiopaque marker 216 comprises a radiopaque material such as platinum or 92% platinum/8% tungsten, and is formed in this particular embodiment by wound flat wire having a first end 218 and a second end 220. The distal radiopaque marker 216 allows the distal end 203 of the composite shaft 200 to be visible by radiography (x-ray) or by fluoroscopy. In other embodiments, the flat wire coil may be replaced by foil or by a cylindrical marker band. In the embodiment of FIG. 4, the first end 218 is just distal to a distal end 222 of the second spiral-wound strand 214, thus avoiding overlap of the distal radiopaque marker 216 and the coil layer 206. In other embodiments, the distal radiopaque marker may comprise round wire and/or may be interwound with the first spiral-wound strand 212 and the second spiral-wound strand 214, for example, within spaces between the first spiral-wound strand 212 and the second spiral-wound strand 214.

Figure 6:
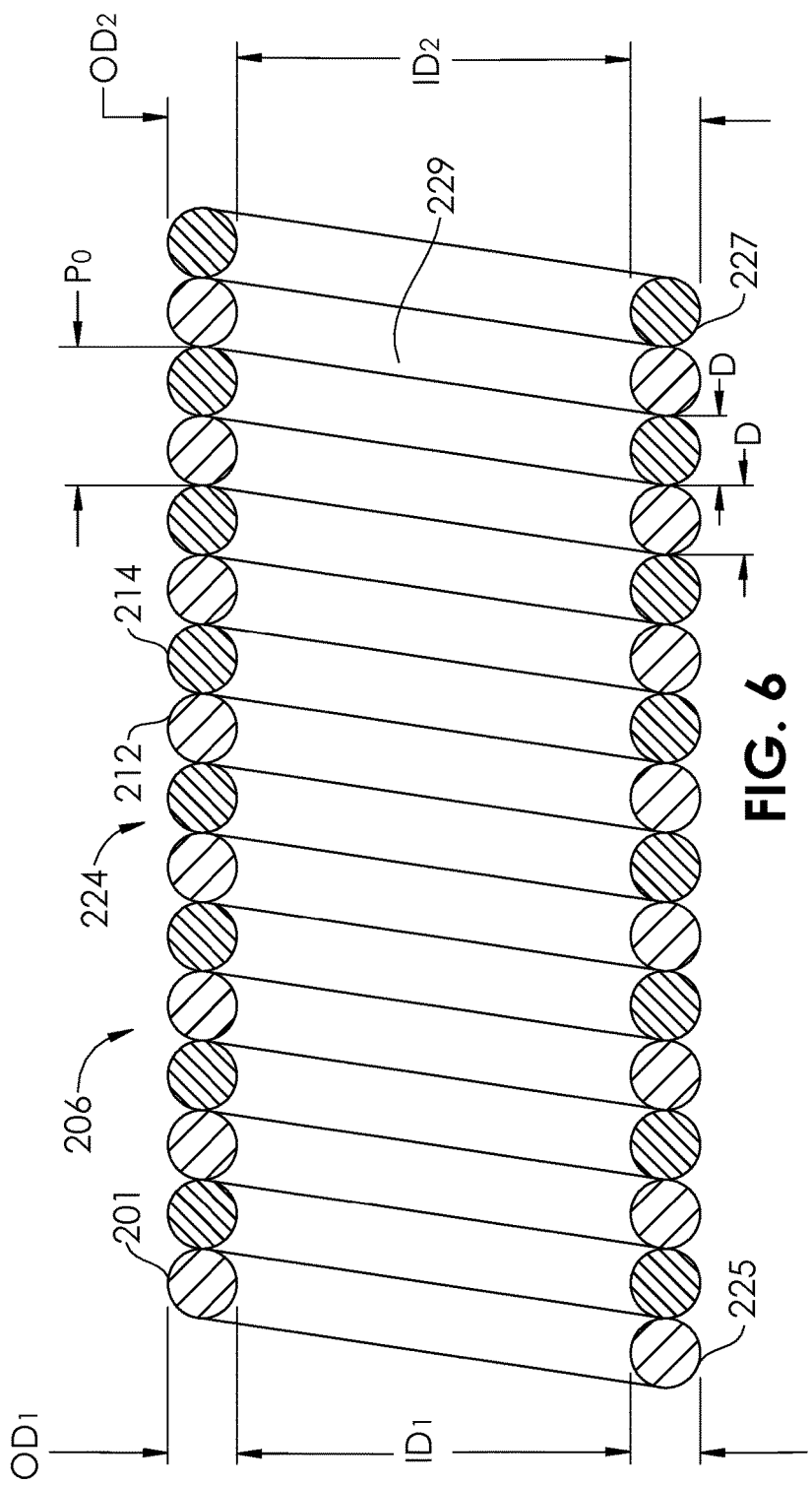
FIG. 6 is a sectional view taken from lines 6-6 of FIG. 5.

FIG. 5 illustrates the coil layer 206 composite coil without the inner polymeric layer 204 or the outer polymeric layer 208, to better indicate the unlike pitch patterns of the first spiral-wound strand 212 and the second spiral-wound strand 214, as further illustrated by FIGS. 6-9. The coil layer 206 has a longitudinally-extending internal cavity 229, which is typically filled by the inner polymeric layer 204 and its lumen 210. FIG. 6 illustrates a proximal close-wound portion 224 of the coil layer 206 having a proximal end 225 and a distal end 227. Each of the first spiral-wound strand 212 and the second spiral-wound strand 214 has a diameter D. The pitch $P_0$ of the coil layer 206 is equal to about 2×D. There may be some slight space between the windings in the close-wound portion, so the pitch $P_0$ may have a value of between 2×D and 2.2×D. In other embodiments, the first spiral-wound strand 212 may have a different diameter from the second spiral-wound strand 214. For example, in a particular embodiment, the first spiral-wound strand 212 has a diameter $D_1$ (or in the case of flat wire, a maximum transverse dimension $D_1$ in the longitudinal direction) and the second spiral-wound strand 214 has a diameter or maximum transverse dimension $D_2$, and the pitch $P_0$ has a value of between $D_1+D_2$ and 1.1×(D1+D2). The close-wound portion 224, by having the adjacent winds of the first spiral-wound strand 212 and the second spiral-wound strand 214 close wound, provides a composite shaft 200 having very good pushability. A longitudinally-directed compressive force placed on the composite shaft 200 at the close-wound portion 224 is transmitted efficiently along the composite shaft 200, as each successive wind pushes on the next. At the close-wound portion 224, the choice of a stiffer material to construct the outer polymeric layer 208, or the choice of a larger outer diameter to construct the outer polymeric layer 208 can further augment the pushability of the composite shaft 200. The outer diameter $OD_1$ of the first spiral-wound strand 212 is greater than the inner diameter $ID_2$ of the second spiral-wound strand 214 and the inner diameter $D_1$ of the first spiral-wound strand 212 is less than the outer diameter $OD_2$ of the second spiral-wound strand 214 (as shown in FIG. 6). Thus, each wind of each of the strands 212, 214 in the close-wound portion 224 has some amount of engagement (diametric overlap).

Figure 7:
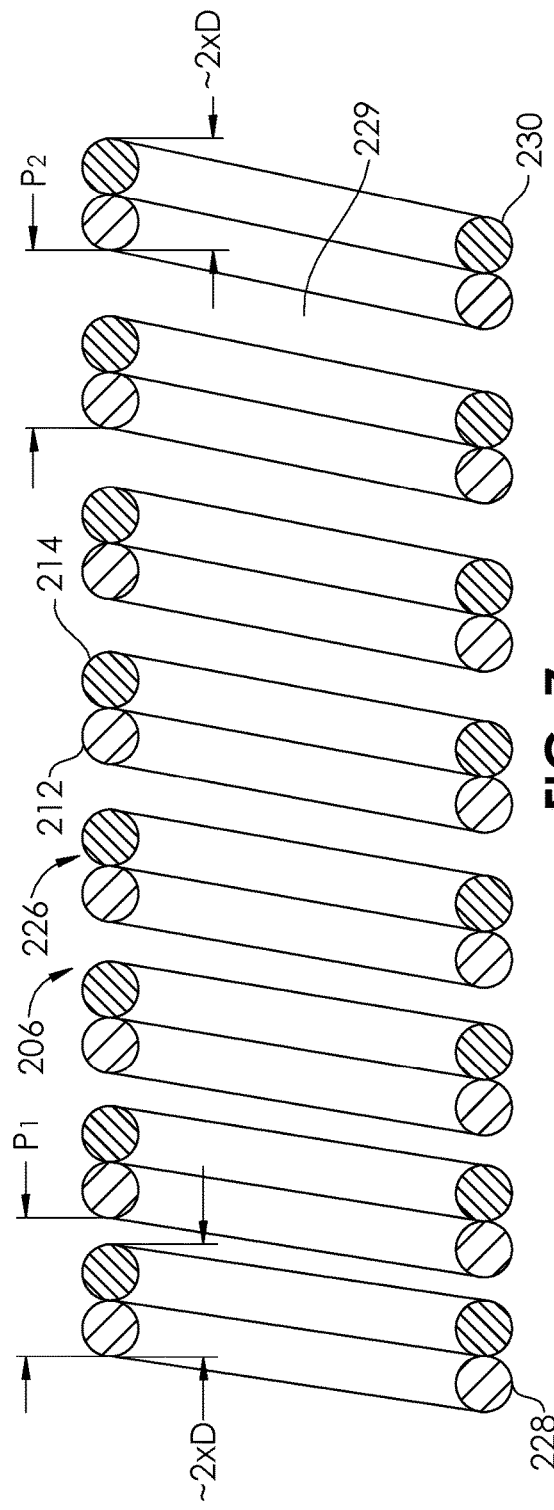
FIG. 7 is a sectional view taken from lines 7-7 of FIG. 5.
Figure 8:
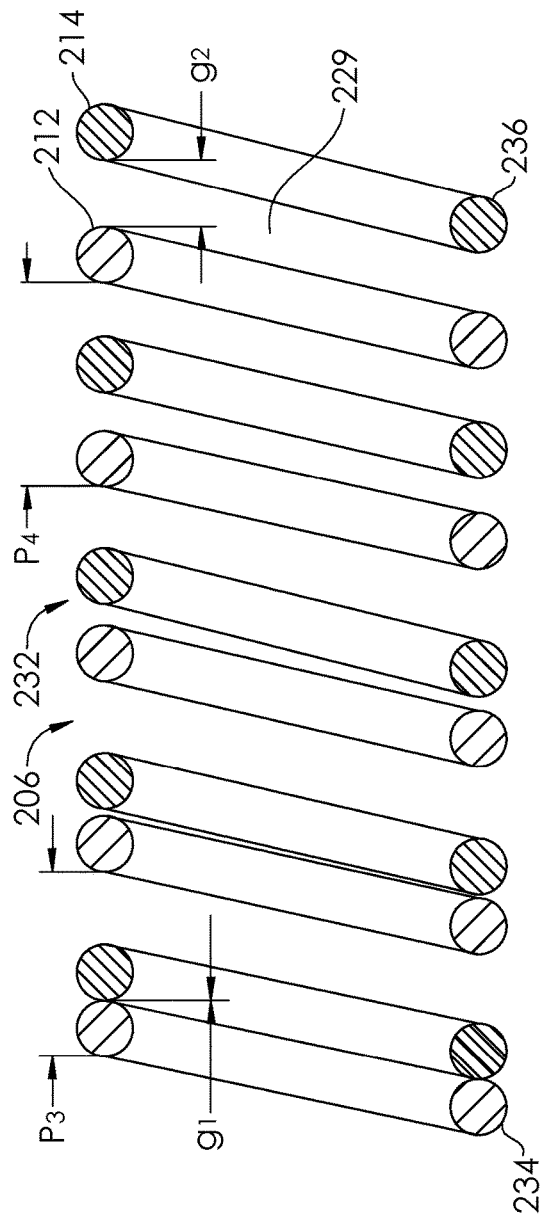
FIG. 8 is a sectional view taken from lines 8-8 of FIG. 5.

FIG. 7 illustrates a first transition portion 226 of the coil layer 206 having a proximal end 228 and a distal end 230. The first spiral-wound strand 212 and the second spiral-wound strand 214 each maintain a similar pitch pattern to each other between the proximal end 228 and the distal end 230 of the first transition portion 226, however, the overall pitch of the bifilar coil of the coil layer 206 changes, increasing from a pitch $P_1$ at the proximal end 228 to a pitch $P_2$ at the distal end 230. In one exemplary embodiment, the first spiral-wound strand 212 and the second spiral-wound strand 214 each comprise wire having a diameter of 0.002 inch; $P_1$ is between about 0.0045 inch and about 0.0055 inch, or about 0.0050 inch; $P_2$ is between about 0.0060 inch and about 0.0080 inch, or about 0.0.0065 inch. FIG. 8 illustrates a second transition portion 232 of the coil layer 206 having a proximal end 234 and a distal end 236. The overall pitch of the bifilar coil of the coil layer 206 continues to increase, changing from a pitch $P_3$ at the proximal end 234 to a pitch $P_4$ at the distal end 236. In addition, however, the first spiral-wound strand 212 and the second spiral-wound strand 214 change from a immediately adjacent state at the proximal end 234, with a separation or gap $g_1$ that is close to zero, to a separation or gap $g_2$ that is up to about one-half of the pitch $P_4$. In one exemplary embodiment, the first spiral-wound strand 212 and the second spiral-wound strand 214 each comprise wire having a diameter of 0.002 inch; $P_3$ is between about 0.0055 inch and about 0.0075 inch, or about 0.0065 inch; $P_4$ is between about 0.0065 inch and about 0.0085 inch, or about 0.0.0075 inch; $g_1$ is between zero and about 0.0004 inch and $g_2$ is between about 0.0030 inch and about 0.0045 inch.

Figure 10:
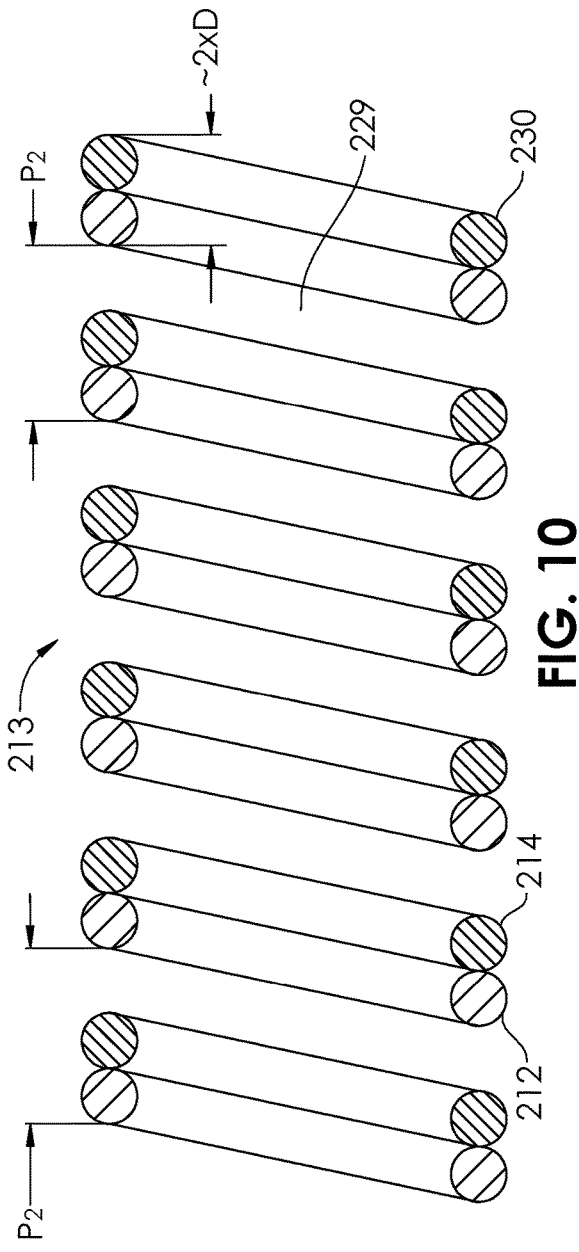
FIG. 10 is a sectional view of an alternative portion of the multifilar coil of FIG. 5, according to an embodiment of the present disclosure.

Thus, returning to FIG. 5, the close-wound portion 224 and the first transition portion 226 together comprise a first section 209 of the coil layer 206 in which the first spiral-wound strand 212 and the second spiral-wound strand 214 have similar pitch patterns as each other. The second transition portion 232 comprises a second section 211 in which the first spiral-wound strand 212 and the second spiral-wound strand 214 have different pitch profiles from each other. In some embodiments, a third section 213 may be provided between the first section 209 and the second section 211, wherein the pitch (e.g., $P_2$) remains constant over a number of winds, as shown in FIG. 10.

Figure 9:
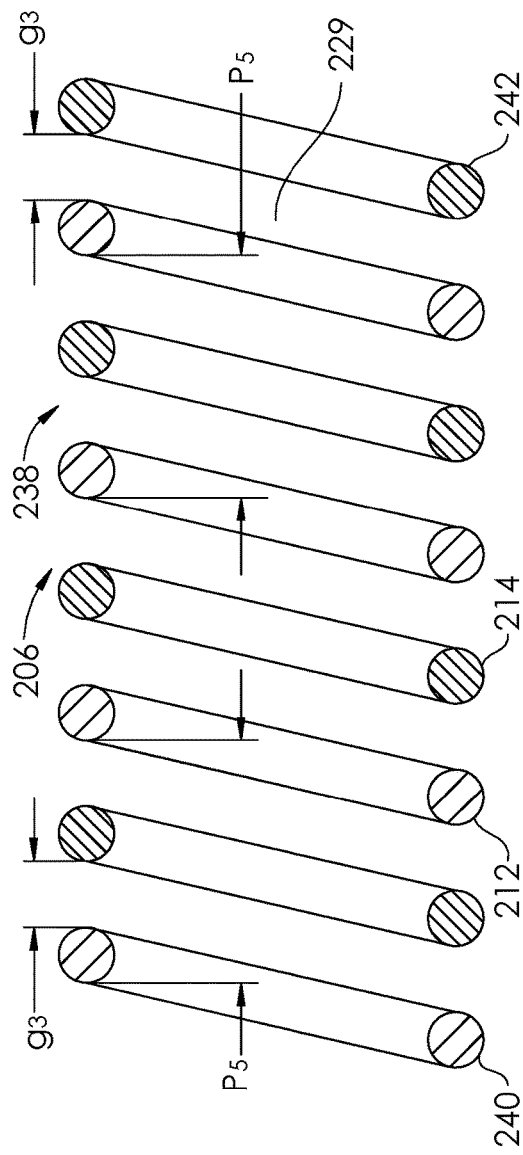
FIG. 9 is a sectional view taken from lines 9-9 of FIG. 5.

FIG. 9 illustrates a distal open-wound portion 238 having a proximal end 240 and a distal end 242. The pitch $P_5$ is constant between the proximal end 240 and the distal end 242. The gap $g_3$ between the first spiral-wound strand 212 and the second spiral-wound strand 214 is constant between the proximal end 240 and the distal end 242. The increase in the gap g in the second transition portion 232 (FIG. 8) is independent from any changes (or lack of changes) in the pitch P of the bifilar coil of the coil layer 206. Thus, the coil layer 206 is able to transition from a proximal close-wound 224 to a distal open-wound portion 238 in a more gradual manner than would a monofilar coil. In addition, the two different transitions of the first transition portion 226 and the second transition portion 232 provide different performance characteristics. For example, the flush arrangement of the first spiral-wound strand 212 and the second spiral-wound strand 214 in the first transition portion 226 can provide more pushability and backup support than the second transition portion 232 (for particular wire materials/transverse dimensions), because of the ability of the first spiral-wound strand 212 and the second spiral-wound strand 214 to push against each other longitudinally. The flush arrangement of the first spiral-wound strand 212 and the second spiral-wound strand 214 in the first transition portion 226 can also provide better torquability than the second transition portion 232, because of the ability of the first spiral-wound strand 212 and the second spiral-wound strand 214 to engage in a screw-like fashion against each other, one helical or curvilinear line or face applying a torque against another curvilinear or helical line or face.

The second transition portion 232, as captured within the composite shaft 200, can provide an increase flexibility than the first transition portion 226, as the decreasing density of wires moving from the proximal end 234 to the distal end 236 creates more space, and thus constrains less the flexure of the inner polymeric layer 204 and/or outer polymeric layer 208. Thus, the composite shaft 200 is able to flex more easily (with less applied force) at the distal end 236 of the second transition portion 232 than at the proximal end 234 of the second transition portion 232 because of both in increase in pitch ($P_4 > P_3$), and the increase in gap ($g_2 > g_1$). There are extra degrees of freedom in transitioning the characteristics of the coil layer 206 along its longitudinal axis 231 (FIG. 5). For example, the transition of the pitch ($P_3$ to $P_4$) can be controlled independently from the transition in gap ($g_1$ to $g_2$) in the second transition portion 232. Thus, abrupt transitions can be avoided or significantly minimized. Abrupt transitions can be a source for a loss of torque delivery (from proximal to distal), especially when the composite shaft 200 is in a tortuous configuration within a body lumen. Abrupt transitions can also be a source for kinking or buckling. By avoiding or minimizing abrupt transitions, smoother, unhindered delivery of a catheter may be achieved. Many current catheters have multiple models, each having a different amount of proximal pushability or support and a different amount of distal flexibility. The smoother, more controllable transitions of these characteristics along the composite shaft 200 may actually allow a smaller number of models of a particular catheter diameter to function in a wider range of clinical conditions. Thus, the composite shaft can provide a "work horse" catheter, which allows users a higher degree of confidence when using it in a particular case, or in a series of cases.

In some embodiments, the pitch increase along the longitudinal axis (pitch increase rate) in the first transition portion 226 and/or the second transition portion 232 may be a constant value. For example, the pitch increase rate may comprise a continuous pitch increase, such as a constant pitch increase rate of about 0.001 inch pitch increase per inch displacement along the longitudinal axis, or any constant value between about 0.0002 and about 0.060, or between about 0.00035 and about 0.040, or between about 0.00045 and about 0.020. Alternatively, in some embodiments, the pitch increase rate, instead of being a constant value, may itself depend on the location along the longitudinal axis. For example, the pitch increase rate may have the following formula:

Pitch Increase Rate (PIR)=$A \times Z$ wherein, A=a constant, and
Z=displacement along the longitudinal axis
In other embodiments, the pitch increase rate may vary along the longitudinal axis in a non-linear manner. For example, by one of the following formulae:

Pitch Increase Rate (PIR)=$A \times Z^2$

Pitch Increase Rate (PIR)=$A \times Z^{1.5}$

Returning to FIG. 8, the increase in the gap g from $g_1$ to $g_2$ in the second transition portion 232 may be similarly represented by a gap increase rate (GIR) that is either a constant value, or is non-constant value (e.g., varying along the longitudinal axis). Alternatively, the increase in the gap g from $g_1$ to $g_2$ in the second transition portion 232 may be represented by a non-similar pitch increase rate between the first spiral-wound strand 212 and the second spiral-wound strand 214. For example, the second spiral-wound strand 214 in the second transition portion shown in FIG. 8 has a larger pitch increase rate than does the first spiral-wound strand 212. The pitch increase rate (inch per inch) of the first spiral-wound strand 212 may be between about 0.0000 and about 0.050, while the pitch increase rate (inch per inch) of the second spiral-wound strand 214 is between about 0.00025 and about 0.060. Alternatively, the pitch increase rate (inch per inch) of the first spiral-wound strand 212 may be between about 0.0002 and about 0.050, while the pitch increase rate (inch per inch) of the second spiral-wound strand 214 is between about 0.00025 and about 0.060. Alternatively, the pitch increase rate (inch per inch) of the first spiral-wound strand 212 may be between about 0.00035 and about 0.030, while the pitch increase rate (inch per inch) of the second spiral-wound strand 214 is between about 0.0004 and about 0.040. Alternatively, the pitch increase rate (inch per inch) of the first spiral-wound strand 212 may be between about 0.00045 and about 0.015, while the pitch increase rate (inch per inch) of the second spiral-wound strand 214 is between about 0.0005 and about 0.020.

In some embodiments, the composite shaft 200 may comprise a coil layer 206 carried over an inner polymeric layer 204, but without an outer polymeric layer 208, similar to what is shown in FIG. 4. The coil layer 206 may be wound onto the inner polymeric layer 204 with sufficient tension, such that the coil layer 206 is sufficiently coupled to the inner polymeric layer 204. In other embodiments, the composite shaft 200 may comprise a coil layer 206 carried within an outer polymeric layer 208, but without an inner polymeric layer 204. The outer polymeric layer 208 may be heat shrunk, overextruded, or even insert molded over the coil layer 206. In either case, a mandrel may be in place within the longitudinally-extending internal cavity 229 of the coil layer 206 when the shrinking, overextruding, or insert molding is performed. The outer polymeric layer 208 can fully embed the coil layer 206, or may allow for some voids surrounding the coil layer 206. Whether the composite shaft includes an inner polymeric layer 204, an outer polymeric layer 208, or both, in some embodiments, the coil layer 206 may actually be embedded within the inner polymeric layer 204, the outer polymeric layer 208, or both.

Figure 18:
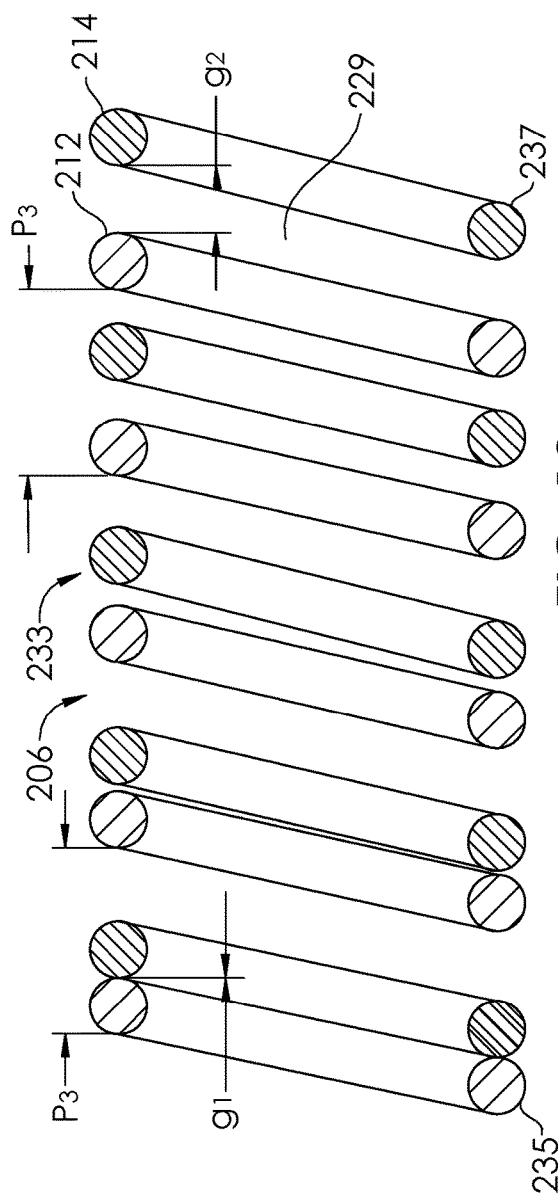
FIG. 18 is a sectional view of an alternative portion of the multifilar coil of FIG. 5, according to an embodiment of the present disclosure.

In an alternative embodiment, the second transition portion 232 of the coil layer 206 of FIG. 8 is replaced by an alternative second transition portion 233 having a proximal end 235 and a distal end 237, as shown in FIG. 18. In this embodiment, the pitch $P_3$ remains the same between the proximal end 235 and the distal end 237, while the gap between the first spiral-wound strand 212 and the second spiral-wound strand 214 increase from gap $g_1$ to gap $g_2$. Again, the first spiral-wound strand 212 and the second spiral-wound strand 214 have different pitch profiles from each other.

FIG. 11 illustrates a composite shaft 250 which may be configured to serve as the tubular shaft 102 of FIG. 1, the tubular shaft 132 of FIG. 2, or another type of medical device shaft. The composite shaft 250 has a proximal end 251 and a distal end 253, and comprises a tubular inner polymeric layer 254, a coil layer 256, and a tubular outer polymeric layer 258. A lumen 260 passes through the composite shaft 250 and has a circular cross-section. In other embodiments, the lumen 260 may have a non-circular cross-section. I still other embodiments, the lumen 260 may comprise two or more lumens. The inner polymeric layer 254 (or "liner") may comprise an extruded tube, and may comprise a number of materials, including lubricious or low-friction materials, such as PTFE, ETFE, or FEP. The inner polymeric layer 254 may also comprise common catheter materials such as polyamide, polyimide, or thermoplastic elastomers, such as polyether block amide. A low friction material may be desirable for constructing the inner polymeric layer 254 if, for example, the lumen 260 is to be used for the passage of a guidewire or of another medical shaft or elongate medical device, such as an embolic coil. The low-friction materials often display "non-stick" characteristics because of their relatively low surface energy. Thus, these materials may be used for constructing the inner polymeric layer 254 when applications involve injecting materials through the lumen 260 wherein good release of the material is desired. These injected materials may include embolic materials such as cyanoacrylate (e.g., N-butyl-2 cyanoacrylate), gelatin foam, polyvinyl alcohol, ethylene vinyl alcohol copolymer, tris-acryl gelatin microspheres, or calcium alginate gel. In other embodiments, a lubricious material may be injected through the lumen 260 to create a low-friction coating. In some embodiments, the material may comprise Baymedix® CL 100 manufactured by Bayer Material Science, LLC of Pittsburgh, Pa., USA. Baymedix is a registered trademark of Covestro Deutschland AG of Leverkusen, Federal Republic of Germany.

The coil layer 256 comprises a multifilar coil which includes two or more different spiral coils. The coil layer 256 is illustrated in FIG. 12 without the inner polymeric layer 254 or the outer polymeric layer 258 (or "jacket"). The coil layer 256 includes a first spiral-wound filament or strand 262 and a second spiral-wound filament or strand 264. In some embodiments, both the first spiral-wound strand 262 and the second spiral-wound strand 264 comprise a metallic material. In other embodiments, both the first spiral-wound strand 262 and the second spiral-wound strand 264 comprise a liquid crystal polymer. In other embodiments, one of the first spiral-wound strand 262 or the second spiral-wound strand 264 comprises a metallic material and the other of the first spiral-wound strand 262 and the second spiral-wound strand 264 comprises a liquid crystal polymer. In the embodiment shown in FIGS. 11-12, the first spiral-wound strand 262 and the second spiral-wound strand 264 each comprise metallic flat wire, though in other embodiments, other materials and other wire cross-sections (round, oval, etc.) may be used, while following a similar winding pattern of the coil layer 256.

In some embodiments, both the first spiral-wound strand 262 and the second spiral-wound strand 264 comprise a round wire. In other embodiments, both the first spiral-wound strand 262 and the second spiral-wound strand 264 comprise a non-round wire, for example, flat wire. In other embodiments, one of the first spiral-wound strand 262 or the second spiral-wound strand 264 comprises a round wire and the other of the first spiral-wound strand 262 and the second spiral-wound strand 264 comprises a non-round wire. In some embodiments, both the first spiral-wound strand 262 and the second spiral-wound strand 264 comprise a highly radiopaque material, such as platinum. In other embodiments, both the first spiral-wound strand 262 and the second spiral-wound strand 264 comprise a high strength material, such as stainless steel. In other embodiments, one of the first spiral-wound strand 262 or the second spiral-wound strand 264 comprises a radiopaque material, such as platinum, and the other of the first spiral-wound strand 262 and the second spiral-wound strand 264 comprises a high strength material, such as stainless steel. The first spiral-wound strand 262 and/or the second spiral-wound strand 264 may comprise platinum, or a platinum alloy, such as 92% platinum. 8% tungsten. In other embodiments, the spiral-wound strand 262 and/or the second spiral-wound strand 264 may comprise a drawn filled tube (DFT®), which may comprise a radiopaque core, such as a platinum core, surrounded by a cylindrical jacket of a high strength material, such as stainless steel, or nickel-titanium alloy.

In some embodiments, both the first spiral-wound strand 262 and the second spiral-wound strand 264 have the same (wound) outer diameter. In other embodiments, the first spiral-wound strand 262 has a different (wound) outer diameter from the second spiral-wound strand 264. In some embodiments, both the first spiral-wound strand 262 and the second spiral-wound strand 264 have the same (wound) inner diameter. In other embodiments, the first spiral-wound strand 262 has a different (wound) inner diameter from the second spiral-wound strand 264. In some embodiments, both the first spiral-wound strand 262 and the second spiral-wound strand 264 are flat wire and have the same maximum transverse dimension (of the flat strand cross-section). In other embodiments, both the first spiral-wound strand 262 and the second spiral-wound strand 264 are flat wire, but have different maximum transverse dimensions (of the flat strand cross-section). In some embodiments, both the first spiral-wound strand 262 and the second spiral-wound strand 264 are round wire and have the same maximum diameter (of the circular strand cross-section). In other embodiments, both the first spiral-wound strand 262 and the second spiral-wound strand 264 are round wire, but have different diameters (of the circular strand cross-section). The diameter or maximum transverse dimension of the wire in the first spiral-wound strand 262 or the second spiral-wound strand 264 may be between about 0.0005 inch and about 0.015 inch, or between about 0.001 inch and about 0.005 inch.

The first spiral-wound strand 262 and the second spiral-wound strand 264 are wound in the same spiral direction (e.g., left-hand or right-hand) as each other, but are constructed with pitch patterns (winding patterns) that differ from each other. The pitch pattern may be completely realized during the winding process, or the pitch pattern may be at least partially created by subsequently stretching or compressing a portion or all of the spiral-wound strand, after it has been initially wound. The coil layer 256 may be treated after being wound. For example, if either of the first spiral-wound strand 262 or the second spiral-wound strand 264 comprises a nickel-titanium alloy or other shape memory material, the wound pattern may be heat set at an elevated temperature, while restrained, in order to impart memory into the wound shape. If either of the first spiral-wound strand 262 of the second spiral-wound strand 264 comprises a heat-treatable material, such as stainless steel, it may be heat treated by exposing it to an elevated temperature.

The first spiral-wound strand 262 and second spiral-wound strand 264 coaxially commingle with each other to embody the multifilar coil of the coil layer 256. The first spiral-wound strand 262 and the second spiral-wound strand 264 are wound, manually, or with a winding machine, together over the inner polymeric layer 254. A mandrel may be inserted down the lumen 260 of the inner polymeric layer 254 to stiffen and support the inner polymeric layer 254 during winding. Alternatively, the first spiral-wound strand 262 may be wound in its entirety over the inner polymeric layer 254, and subsequently, the second spiral-wound strand 264 may be wound in its entirety over the inner polymeric layer 254. In other embodiments, the first spiral-wound strand 262 and the second spiral-wound strand 264 may be wound over a mandrel, the mandrel subsequently removed, and the inner polymeric layer 254 inserted through the joint inner lumen of the first spiral-wound strand 262 and the second spiral-wound strand 264. In still other embodiments, the first spiral-wound strand 262 may be wound over and mandrel, the second spiral-wound strand 264 may be wound separately over a mandrel, the first spiral-wound strand 262 and the second spiral-wound strand 26 may each have their mandrels removed and the first spiral-wound strand 262 and the second spiral-wound strand 264 may be manipulated so that they are fit together. Subsequently, the inner polymeric layer 254 is inserted through the joint inner lumen of the first spiral-wound strand 262 and the second spiral-wound strand 264.

Each successive wind of the coil layer 256 comprises a different alternating strand (first spiral-wound strand 262, second spiral-wound strand 264, first spiral-wound strand 262, second spiral-wound strand 264, etc.). Though the embodiment of FIGS. 11-12 comprises a bifilar coil, in alternative embodiments that are trifilar, quadrifilar, or more, the alternating strands would also be a feature. For example, in a trifilar coil, the strands would alternate as follows: first spiral-wound strand, second spiral-wound strand, third spiral-wound strand, first spiral-wound strand, second spiral-wound strand, third spiral-wound strand, etc. A distal radiopaque marker may also be used on the coil layer 256, such as the distal radiopaque marker 216 of the coil layer 206, or any of its alternative embodiments.

Figure 13:
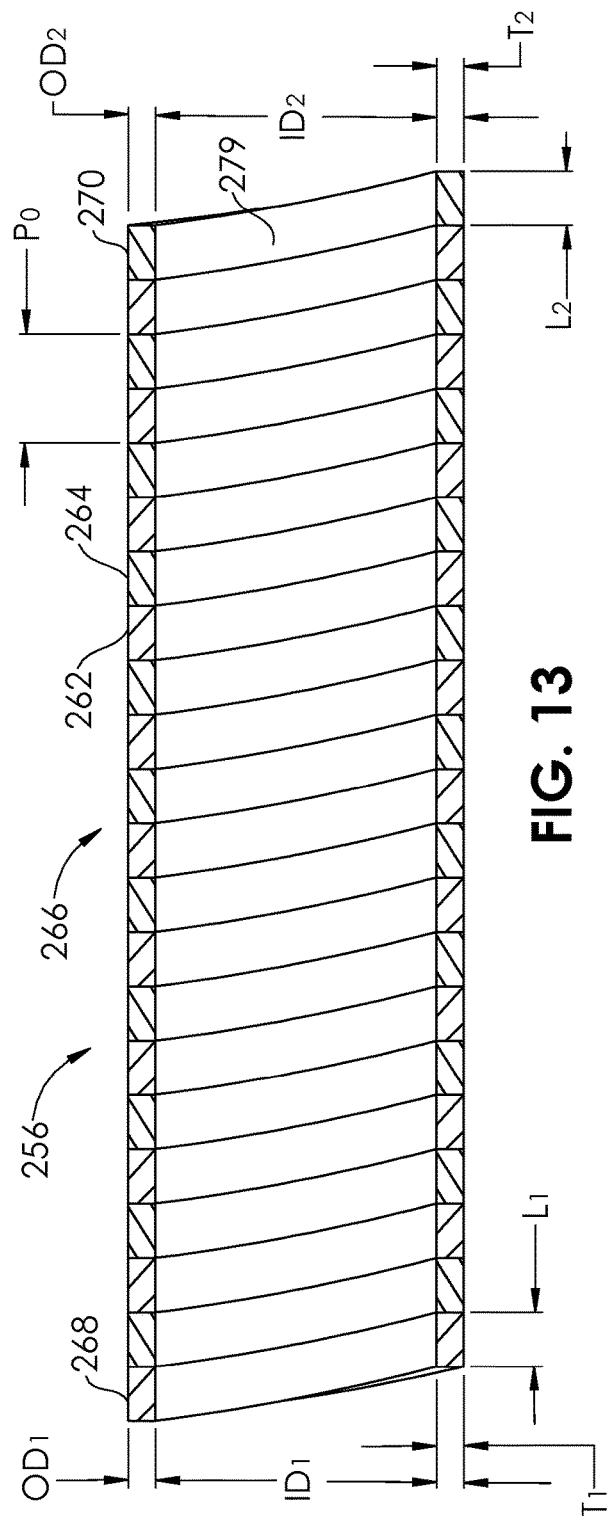
FIG. 13 is as sectional view taken from lines 13-13 of FIG. 12.

The coil layer 256 has a longitudinally-extending internal cavity 279, which is typically filled by the inner polymeric layer 254 and its lumen 260. FIG. 13 illustrates a proximal close-wound portion 266 of the coil layer 256 having a proximal end 268 and a distal end 270. Each of the first spiral-wound strand 262 and the second spiral-wound strand 264 has a cross-sectional length L and thickness T. the length L is configured to extend generally in the longitudinal direction of the coil layer 256 when wound and the thickness T is configured to extend radially. In the embodiment of FIGS. 11-17, the length L is larger than the thickness T, and, because the cross-section is generally rectangular, the length T is the maximum transverse dimension. The length L may range between about 0.002 inch and about 0.020 inch and the thickness T may range from between about 0.0005 inch and about 0.005 inch. The pitch $P_0$ of the coil layer 256 is equal to about 2×L. The inner diameter ID of the coil layer 256 is equal to about OD −2×T, where OD is the outer diameter of the coil layer 256. There may be some slight space between the windings in the close-wound portion, so the pitch $P_0$ may have a value of between 2×L and 2.2×L. In other embodiments, the first spiral-wound strand 262 may have a different length $L_1$ and/or thickness $T_1$ from the second spiral-wound strand 264 ($T_2$, $L_2$). For example, in a particular embodiment, the first spiral-wound strand 262 has a maximum transverse dimension ($L_1$) and the second spiral-wound strand 214 has a maximum transverse dimension ($L_2$), and the pitch $P_0$ has a value of between $L_1+L_2$ and 1.1×(L1+L2). The close-wound portion 266, by having the adjacent winds of the first spiral-wound strand 262 and the second spiral-wound strand 264 close wound, provides a composite shaft 250 having very good pushability. A longitudinally-directed compressive force placed on the composite shaft 250 at the close-wound portion 224 is transmitted efficiently along the composite shaft 250, as each successive wind pushes on the next. At the close-wound portion 266, the choice of a stiffer material to construct the outer polymeric layer 258, or the choice of a larger outer diameter to construct the outer polymeric layer 258 can further augment the pushability of the composite shaft 250. The outer diameter $OD_1$ of the first spiral-wound strand 262 is greater than the inner diameter $ID_2$ of the second spiral-wound strand 264 and the inner diameter $ID_1$ of the first spiral-wound strand 262 is less than the outer diameter $OD_2$ of the second spiral-wound strand 264 (as shown in FIG. 13). Thus, each wind of each of the strands 262, 264 in the close-wound portion 266 has some amount of engagement (diametric overlap).

Figure 14:
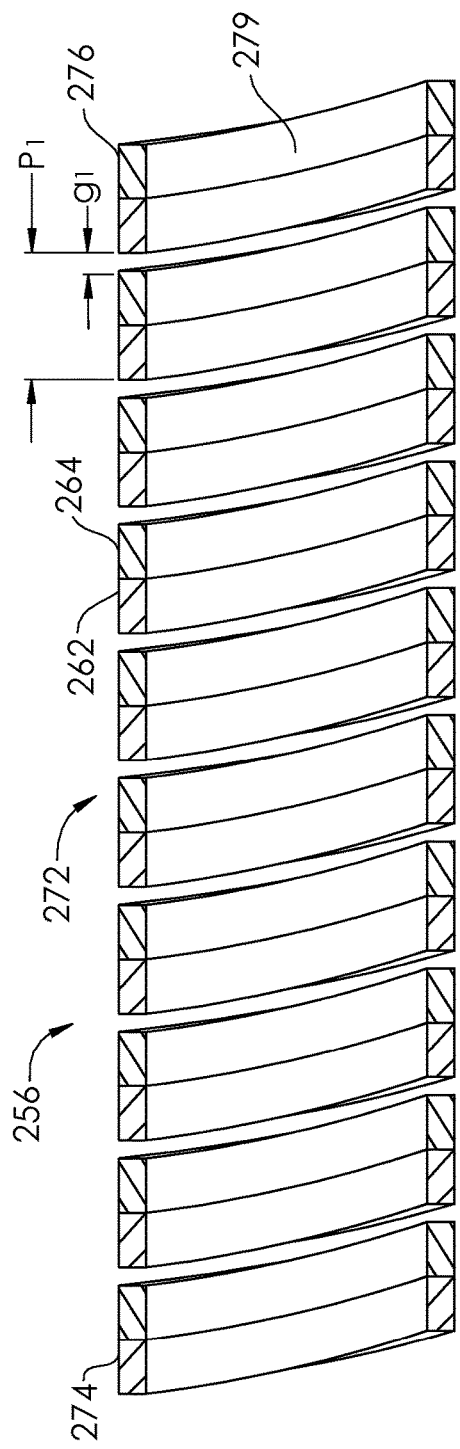
FIG. 14 is as sectional view taken from lines 14-14 of FIG. 12.

FIG. 14 illustrates a first open pitch portion 272 of the coil layer 256 having a proximal end 274 and a distal end 276. The first spiral-wound strand 262 and the second spiral-wound strand 264 each maintain a similar pitch pattern to each other between the proximal end 274 and the distal end 276 of the first open pitch portion 272, and is a constant pitch $P_1$. The pitch $P_1$ is equal to the pitch $P_0$ (FIG. 13) plus a gap $g_1$. In one exemplary embodiment, the first spiral-wound strand 262 and the second spiral-wound strand 264 each comprise wire having a cross-section with a length L of 0.003 inch and a thickness T of 0.001 inch; $P_0$ is about 0.0060 inch; $P_1$ is between about 0.0065 inch and about 0.0075 inch, or about 0.0070 inch; $g_1$ is between about 0.0005 inch and about 0.0015 inch, or about 0.0.0010 inch. Returning to FIG. 12, in between the proximal close-wound portion 266 and the first open-wound portion 272 is a short transition region 278. The pitch increases from pitch $P_0$ to pitch $P_1$ over the short transition region 278. The pitch may transition from pitch $P_0$ to pitch $P_1$ over as little as one wind, or even less than a wind. However, the short transition region 278 behaves generally like the first transition portion 226 of FIG. 7.

FIG. 15 illustrates a second open pitch portion 280 of the coil layer 256 having a proximal end 282 and a distal end 284. The first spiral-wound strand 262 and the second spiral-wound strand 264 each maintain a similar pitch pattern to each other between the proximal end 282 and the distal end 284 of the second open pitch portion 280, and it is a constant pitch $P_2$. The pitch $P_2$ is equal to the pitch $P_0$ (FIG. 13) plus a gap $g_2$. Returning to FIG. 12, in between the first open-wound portion 272 and the second open-wound portion 280 is a short transition region 282. The pitch increases from pitch $P_1$ to pitch $P_2$ over the short transition region 282. The pitch may transition from pitch $P_1$ to pitch $P_2$ over as little as one wind, or even less than a wind. However, the short transition region 282 behaves generally like the first transition portion 226 of FIG. 7.

FIG. 16 illustrates a third open pitch portion 286 of the coil layer 256 having a proximal end 288 and a distal end 290. The first spiral-wound strand 262 and the second spiral-wound strand 264 each maintain a similar pitch pattern to each other between the proximal end 288 and the distal end 290 of the third open pitch portion 286, and it is a constant pitch $P_3$. A similar gap $g_2$ exists between successive winds of the bifilar combination of the first spiral-wound strand 262 and the second spiral-wound strand 264 as the gap $g_2$ in the second open pitch portion 280 of FIG. 15. However, an additional gap $g_3$ has been formed between the first spiral-wound strand 262 and the second spiral-wound strand 264. The pitch $P_3$ is equal to the pitch $P_0$ (FIG. 13), plus gap $g_2$, plus gap $g_3$. Returning to FIG. 12, in between the second open-wound portion 280 and the third open-wound portion 286 is a short transition region 292. The pitch increases from pitch $P_2$ to pitch $P_3$ over the short transition region 292. The pitch may transition from pitch $P_2$ to pitch $P_3$ over as little as one wind, or even less than a wind. However, the short transition region 292 behaves generally like the first transition portion 226 of FIG. 7.

Figure 17:
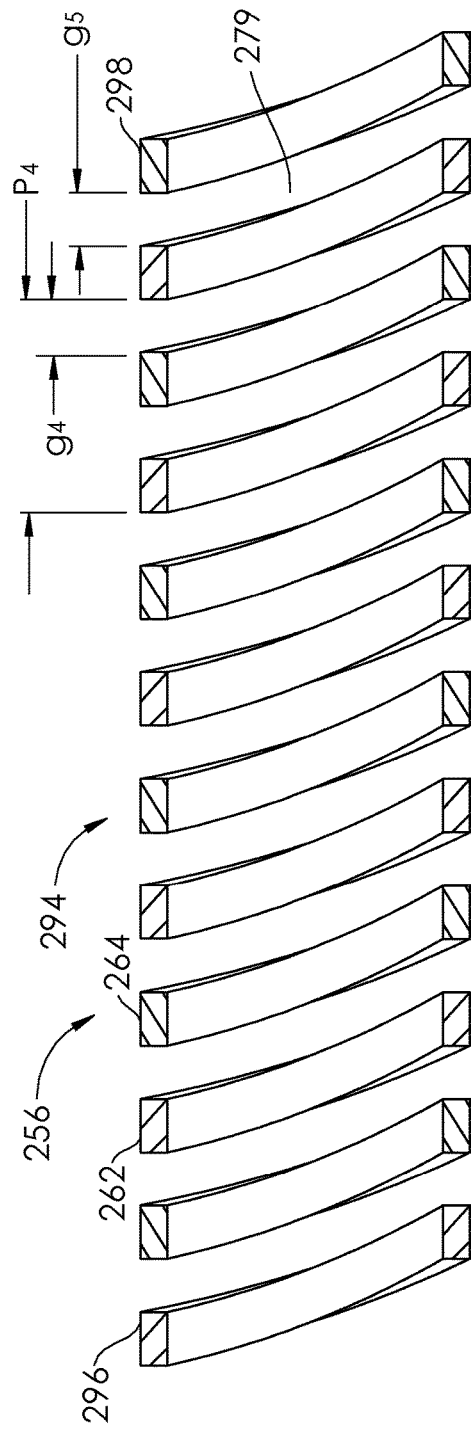
FIG. 17 is as sectional view taken from lines 17-17 of FIG. 12.

FIG. 17 illustrates a fourth open pitch portion 294 of the coil layer 256 having a proximal end 296 and a distal end 298. The first spiral-wound strand 262 and the second spiral-wound strand 264 each maintain a similar pitch pattern to each other between the proximal end 296 and the distal end 298 of the fourth open pitch portion 294, and it is a constant pitch $P_4$. A constant gap $g_4$ exists between successive winds of the bifilar combination of the first spiral-wound strand 262 and the second spiral-wound strand 264. An increased gap $g_5$ (greater than $g_3$) has been formed between the first spiral-wound strand 262 and the second spiral-wound strand 264. The pitch $P_4$ is equal to the pitch $P_0$ (FIG. 13), plus gap $g_4$, plus gap $g_5$. Returning to FIG. 12, in between the third open-wound portion 286 and the fourth open-wound portion 294 is a short transition region 299. The pitch increases from pitch $P_3$ to pitch $P_4$ over the short transition region 299. The pitch may transition from pitch $P_3$ to pitch $P_4$ over as little as one wind, or even less than a wind. However, the short transition region 299 behaves generally like the first transition portion 226 of FIG. 7.

Figure 19:
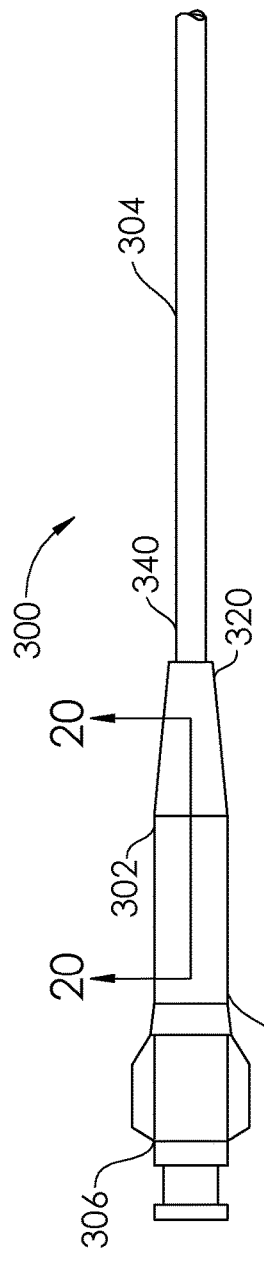
FIG. 19 is a plan view of the proximal end of a catheter, according to an embodiment of the present disclosure.
Figure 20:
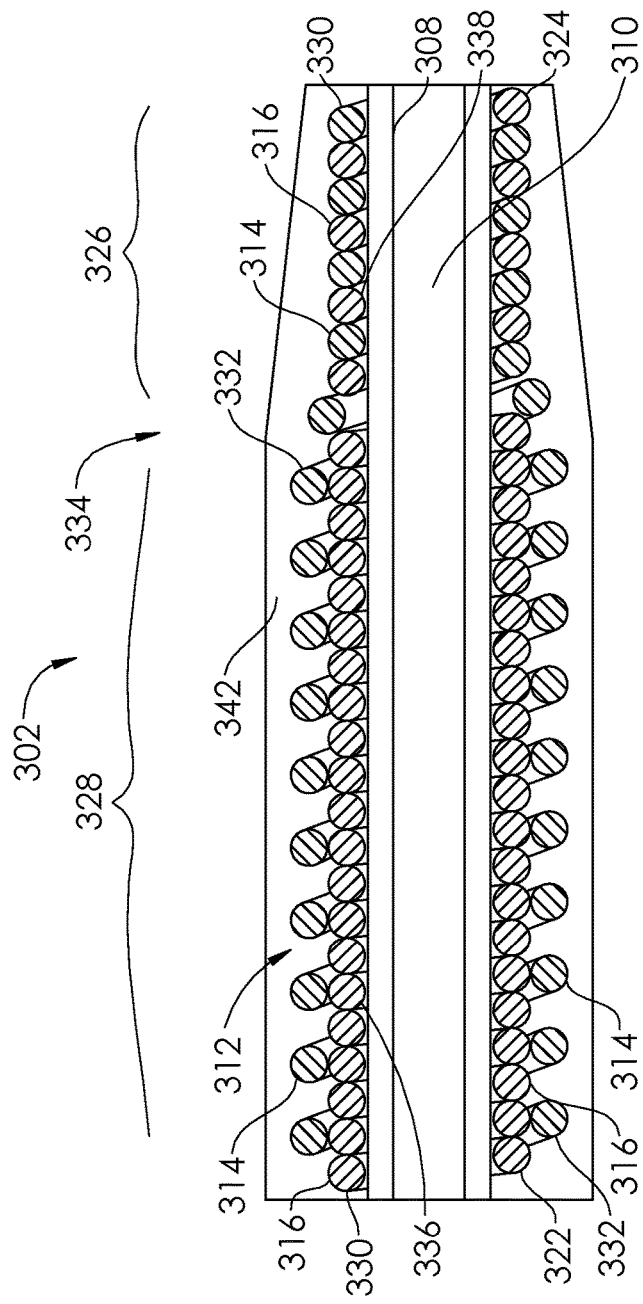
FIG. 20 is a sectional view taken from lines 20-20 of FIG. 19.

In an alternative embodiment, show in FIGS. 19-20, a catheter 300 comprises a catheter shaft 304, a hub 306, and strain relief 302 having a proximal end 318 and a distal end 320. The catheter 300 may be a microcatheter, a guiding catheter, a guide sheath, or any other catheter having the need for strain relief, including the microcatheter 100 of FIG. 1, the guiding catheter 130 of FIG. 2, and any of their embodiments described herein. The strain relief 302 includes a tubular inner polymeric layer 308 having a lumen 310 extending therethrough. A multilayer coil 312, having a proximal end 322 and a distal end 324, is wound over the inner polymeric layer 308, and comprises a first coiled strand 314 and a second coiled strand 316. The first coiled strand 314 and the second coiled strand 316 are both wound in the same direction as each other (e.g., left-hand or right-hand). In some embodiments, both the first coiled strand 314 and the second coiled strand 316 comprise a metallic material. In other embodiments, both the first coiled strand 314 and the second coiled strand 316 comprise a liquid crystal polymer. In other embodiments, one of the first coiled strand 314 or the second coiled strand 316 comprises a metallic material and the other the first coiled strand 314 or the second coiled strand 316 comprises a liquid crystal polymer. In some embodiments, both the first coiled strand 314 and the second coiled strand 316 are flat wire and have the same maximum transverse dimension (of the flat strand cross-section). In other embodiments, both the first coiled strand 314 and the second coiled strand 316 are flat wire, but have different maximum transverse dimensions (of the flat strand cross-section). In some embodiments, both the first coiled strand 314 and the second coiled strand 316 are round wire and have the same maximum diameter (of the circular strand cross-section). In other embodiments, both the first coiled strand 314 and the second coiled strand 316 are round wire, but have different diameters (of the circular strand cross-section). The diameter or maximum transverse dimension of the wire in the first coiled strand 314 or the second coiled strand 316 may be between about 0.0005 inch and about 0.015 inch, or between about 0.001 inch and about 0.005 inch.

The first coiled strand 314 and the second coiled strand 316 coaxially commingle with each other at an inner layer 330 over a distal portion 326 of the multilayer coil 312, but in a proximal portion 328 of the multilayer coil 312 the second coiled strand 316 comprises the inner layer 330, while the first coiled strand 314 comprises an outer layer 332, which is wound over the inner layer 330. A transition portion 334, located between the proximal portion 328 and the distal portion 326, allows the first coiled strand 314 to transition between the inner layer 330 at the distal portion 326 and the outer layer 332 at the proximal portion 328. The transition portion 334 also allows the second coiled strand 316 to transition between a close-wound pitch pattern 336 in the proximal portion 328 and an open-wound pitch pattern 338 in the distal portion 326. At the proximal portion 328, the combination of the close-wound pitch pattern 336 of the second coiled strand 316 in the inner layer 330 and the overlap (overwind) of the first coiled strand 314 of the outer layer 332 creates a stiffer, robust transition from the hub 306 to the distal portion 326. The single inner layer 330 at the distal portion 326 creates a transition between the proximal portion 328 and the proximal end 340 (FIG. 19) of the catheter shaft 304.

The multilayer coil 312 has a seamless coaxial branching between a single layer coil distally and a two-layer coil proximally, with no wire ends necessary between the proximal end 322 and the distal end 324. An outer layer 342 comprising a soft, flexible material (e.g., silicone, thermoplastic elastomer, or other elastomer) is molded over the inner polymeric layer 308 and the multilayer coil 312. In some embodiments, the outer layer 342 may be expanded (with solvents or radial stretching) and may be allowed to collapse over the inner polymeric layer 308 and the multilayer coil 312. In some embodiments, the multilayer coil 312 and the outer layer 342 may be applied over the composite shafts 200, 250 described herein. The strain relief 302 having the multilayer coil 312 may in some embodiments also be used at other parts of a catheter shaft, not only as a strain relief. In some alternate embodiments, there may actually be a longitudinal transition from dual layer to single layer and back to dual layer. In other embodiments, there may be more than two layers of coil, for example three layers, four layers, or more.

FIGS. 21-22 illustrate a general construction of a machine 400 for winding the composite coils 206, 256 described in relation to the embodiments herein, or other composite coils. The machine 400 is illustrated in FIG. 21 for automated use, but may be partially automated/partially manual, fully automated, or fully manual. The machine 400 comprises a base 402 configured to rest on a table top or to be supported on a table or on legs. The base 402 may alternatively be suspended from a ceiling or attached to a wall or frame. A sliding stage 404 is configured to slide along an axis $x_1$ in a positive or negative direction. The sliding stage 404 is displaced along the axis $x_1$ in relation to the base 402 by a first lead screw 406, which is driven by a first motor 408. The first lead screw 406 engages with a half-nut or other engagement member (not shown) that is coupled to the sliding stage 404 (e.g., underneath). A first channel 401 on the base 402 and a second channel 403 under the sliding stage 404 provide a space for the first lead screw 406 and the engagement member. The sliding stage 404 has a first side 410 supporting a wire feeding assembly 412 and a second side 414, opposite the first side 410, the second side 414 supporting a wire engagement assembly 416.

Adjacent the sliding stage 404, a mandrel rotation assembly 418 is carried on the base 402. Thus, the wire feeding assembly 412 and the wire engagement assembly 416 are configured to move with the sliding stage 404 along axis $x_1$, in relation to the base 402, while the mandrel rotation assembly 418 remains with the base 402. The mandrel rotation assembly 418 comprises a mandrel 420, which is releasably gripped on its first end 422 by a first chuck 424, and on its second end 426 by a second chuck 428. The first chuck 424 is attached to a first sliding base 430, that is coupled to the base 402 by a slide 432. The second chuck 428 is attached to a second sliding base 434, that is coupled to the base 402 by a slide 436. The first and second sliding bases 430, 434 may be locked at any position along axis $x_2$, or unlocked, by tightening screws 438, 440 (knobbed screws, thumb screws, etc.). In other embodiments, the tightening screws 438, 440 may be replaced by knobs of micrometers that control the adjustment of the first and second sliding bases 430, 434 in relation to the base 402, or may even be replaced by motors that drive the adjustment of the first and second sliding bases 430, 434 in relation to the base 402. The tension of the mandrel 420 can be controlled by the adjustment of the first and second sliding bases 430, 434 along axis $x_2$. Actually, only one of the first and second sliding bases 430, 434 need be moveable along axis $x_2$ to allow the variance of tension in the mandrel 420. The other of the first and second sliding bases 430, 434 may be statically held to the base 402. Second motor 442 and third motor 444 are carried on the first and second sliding bases 430, 434, to control rotation of the first and second chucks 424, 428, respectively. The second and third motors 442, 444 can be stepper motors, programmed to rotate in unison with each other, so that the first end 422 and the second end 426 of the mandrel 420 are caused to rotate in unison. A multifilar coil/composite coil is being wound by the machine 400 directly onto the mandrel 420, or, for example, wound over an inner polymeric layer 204, 254, 308. Though not shown in FIGS. 21-22, in case wherein the coil is wound over an inner polymeric layer 204, 254, 308, the inner polymeric layer 204, 254, 308 (and mandrel 420) are secured together to the first and second chucks 424, 428.

The wire feeding assembly 412 comprises a first spool 446 and a second spool 448 (e.g., of wire/filament/strand/drawn filled tube) which are carried, respectively, on a first holder 450 and a second holder 452. The first spool 446 and second spool 448 supply first unwound strand 447 and second unwound strand 449, respectively. The first and second holders 450, 452 are adjustable along axis $x_3$ via a channel 454. The first and second spools 446, 448 and first and second holders 450, 452 may be replaced by three spools and three holders, four spools and four holders, or more, to allow for trifilar, quadifilar, etc. coils to be constructed. In some embodiments, two or more spools may be carried on one holder. The first and second holders 450, 452 have adjustable friction elements 456, 458, to control the rotation of the first and second spools 446, 448 when the first and second strands 447, 449 are wound onto the mandrel 420. In some embodiments, the first and second holders 450, 452 may also or alternatively include one-way ratchets. In some embodiments, the first and second spools 446, 448 may each be rotated on the first and second holders 450, 452 by an individual motor, e.g., a stepper motor that is synched with the rotation of the first and second chucks 424, 428, or even controlled (e.g., by a controller) via feedback from measured tension allied on the first and second holders 450, 452 by the first and second spools 446, 448.

The wire engagement assembly 416 comprises a base 460 carried on the sliding stage 404. A first engagement arm 462 is carried on the base 460 and a second engagement arm 464 is movably carried on the base 460. The second engagement arm 464 is adjustable along axis $x_4$ in relation to the first engagement arm 462. In some embodiments, both the first engagement arm 462 and the second engagement arm 464 are adjustable in relation to the base 460, but in the embodiment illustrated in FIGS. 21-22, only the second engagement arm 464 is adjustable in relation to the base 460. A second lead screw 466 is configured to slide the second engagement arm 464 along axis $x_4$ in either direction (positive or negative). A fourth motor 468 is coupled to the base 460 and is configured to turn the second lead screw 466. The first engagement arm 462 controls the longitudinal (along axis $x_2$) point of application of strand 447 on the mandrel 420 via first engagement pin 463, coupled to the first engagement arm 462. The second engagement arm 464 controls the longitudinal (along axis $x_2$) point of application of strand 449 on the mandrel 420 via second engagement pin 465, coupled to the second engagement arm 464. Thus, as the mandrel 420 is turned by the second and third motors 442, 444 and/or first and second chucks 424, 428, The first motor 408 controls the movement of the sliding stage 404 (and thus the base 460) along axis $x_1$ to move strands 447, 449 as they are wound. The rotational speed of the first and second chucks 424, 428 and the longitudinal speed of the sliding stage 404 completely defines the pitch of the strand 447. The rotational speed of the first and second chucks 424, 428 and the longitudinal speed of the sliding stage 404, combined with the relative longitudinal speed of the second engagement arm 464 along axis $x_4$ in relation to the base 460/sliding stage 404 defines the pitch of the strand 449. Thus, the addition of the relative longitudinal displacement between the second engagement arm 464 and the first engagement arm 462 allows the first strand 447 and the second strand 449 to be wound with different pitch patterns from each other.

As shown in more detail in FIG. 22, a first guiding pin 470 is coupled to the first engagement arm 462, and a second guiding pin 474 is coupled to the second engagement arm 464. The strand 447 engages the outside 472 of first guiding pin 470 and the inside 476 of the first engagement pin 463. The strand 449 engages the outside 476 of second guiding pin 474 and the inside 478 of the second engagement pin 465. The inside 476 (e.g. maximum diameter along axis $x_2$ in the positive direction) of first engagement pin 463 is flush or extends further than the inner edge 480 of the first engagement arm 462. The inside 478 (e.g. maximum diameter along axis $x_2$ in the negative direction) of second engagement pin 465 is flush or extends further than the inner edge 482 of the second engagement arm 464. Thus, the inside 476 of the first engagement pin 463 and the inside 478 of the second engagement pin 465 can be adjusted until the distance between them is zero (when no strands are present), or the distance between them is equal to the diameter of the strand 447 plus the diameter of the strand 449. Thus, the two strands 447, 449 may be wound with a gap of substantially zero between them. The first engagement arm 462 and second engagement arm 464 at their closest would likely be adjusted such that the inside 476 of the first engagement pin 463 and the inside 478 of the second engagement pin 465 have slightly more distance between them than the diameter of the strand 447 plus the diameter of the strand 449, so that the strands 447, 449 are not pinched between the first and second engagement pins 463, 465.

A control box 484 is coupled to the rest of the machine 400 via a cable 486, which may include power supply and information transfer (bi-directional). Internal wiring (not shown) may distribute the power or information to or from any of the internal components of the machine 400. The control box 484 includes a power cord 488 for coupling to a wall power source. The control box 484 is shown in more detail in FIG. 23. A controller 490 is configured to control any of the motors 408, 442, 444, 468 or other controllable components of the machine 400. The controller 490 may comprise a microcontroller. A memory 492 may comprise a non-transitory signal comprising instructions executable by a processor 494 for operating any one or more of the motors 408, 442, 444, 468 or other components of the machine 400. Any one or more of the motors 408, 442, 444, 468 (or others) may comprise stepper motors. The processor 494 may comprise a microprocessor, and may be configured to make calculations, and receive data, either from internal components (force sensor, pressure sensor, temperature sensor, etc.) or from external output. A user interface 496 may comprises a GUI (graphical user interface) or one or more buttons, and may include a touch-sensitive screen, such as a resistive or capacitive touch-sensitive screen. In use, data may be input by a user via the user interface 496 to the memory 492 or to an element of the processor 494. A display 498 may comprise a portion of the user interface 496 or may be a separate component. The display 498 may display graphic data, or text. The display 498 may be augmented or replaced by an audio speaker that supplies verbal information.

Figures 23, 24:
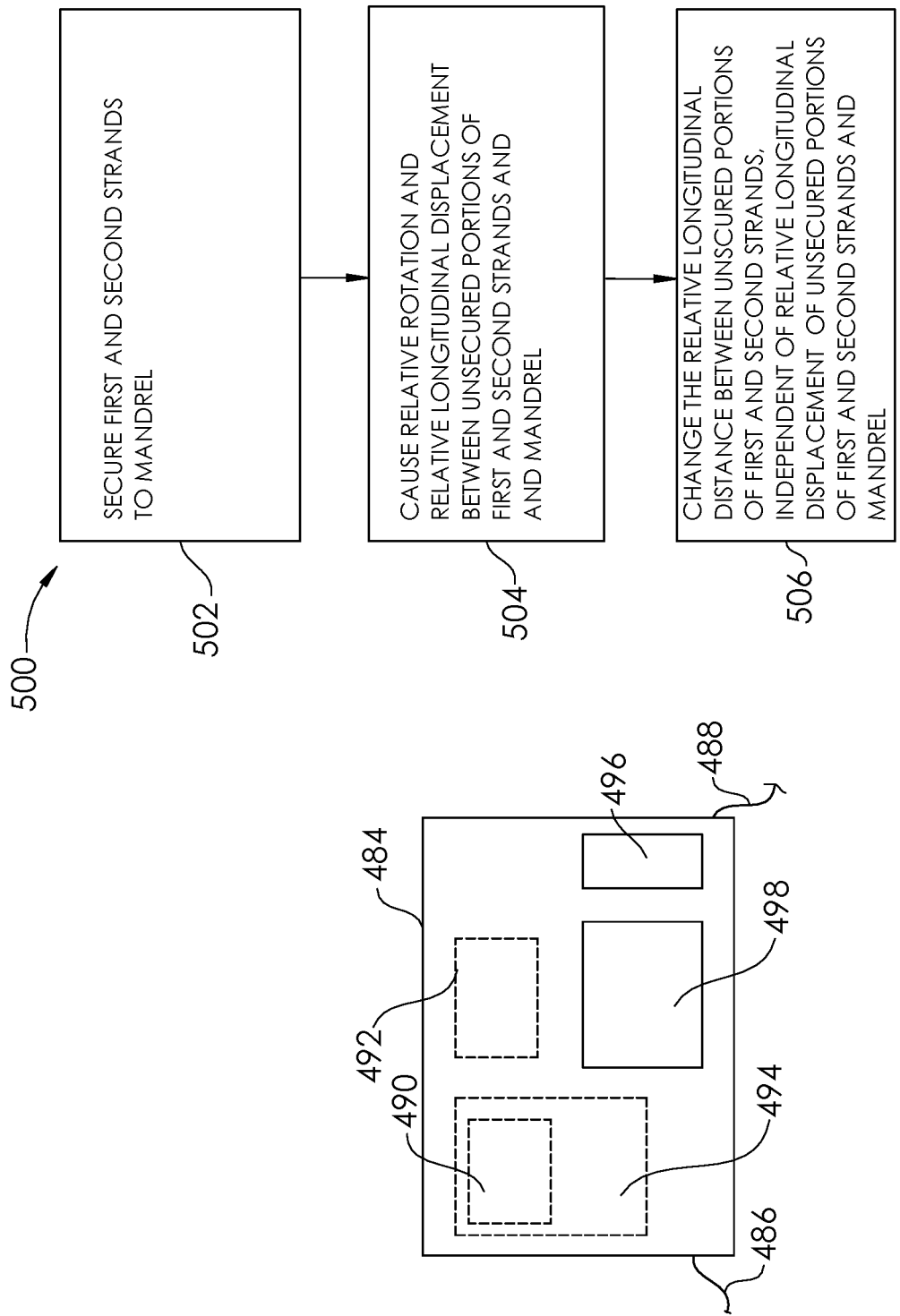
FIG. 23 is a plan view of a control box of the machine of FIG. 21, according to an embodiment of the present disclosure.
FIG. 24 is a block diagram of a method of making a multifilar coil.

A method 500 for making a multifilar coil is illustrated in FIG. 24. In a first step 502 of the method 500, the first strand 447 is secured to the mandrel 420 and the second strand 449 is secured to the mandrel 420. The strands 447, 449 may be secured directly to the mandrel 420, or may be secured to an inner polymeric layer 204, 254, 308 having a mandrel 420 placed therethrough. In some embodiments, if the medical shaft does not have an inner lumen, it may be sufficiently stiff enough such that a mandrel 420 is not required. The strands 447, 449 may be secured, for example to the first end 422 of the mandrel 420 or to the second end 426, with tape, adhesive, epoxy, a weld, or other manners of joining. The points of securement can be left in place, or may later be undone or cut. In a second step 504, relative rotation of the mandrel 420 (and/or medical shaft) in relation to an unsecured portion 451 (FIG. 22) of the first strand 447 and an unsecured portion 453 (FIG. 22) of the second strand 449 is caused and relative longitudinal displacement of the mandrel 420 (and/or medical shaft) in relation to an unsecured portion 451 of the first strand 447 and an unsecured portion 453 of the second strand 449 is caused. In some embodiments, the mandrel 420 may be rotated, but in other embodiments, the unsecured portions 451, 453 of the first strand 447 and second strand 449 may be rotated around a non-rotating mandrel 420. In other embodiments both the unsecured portions 451, 453 of the first and second strands 447, 449 and the mandrel 420 may be rotated (e.g., in opposite rotational direction from each other). The relative longitudinal displacement between the mandrel 420 and the unsecured portions 451, 453 of the first and second strands 447, 449 may be caused by moving only the unsecured portions 451, 453 of the first and second strands 447, 449 in a longitudinal direction (either direction), or in other embodiments by moving the mandrel 420 in a longitudinal direction, or in other embodiments, by moving both the mandrel 420 and the unsecured portions 451, 453 of the first and second strands 447, 449. The combination of the relative rotation and the relative longitudinal displacement causes each of the first strand 447 and second strand 449 to form a helical shape. The particular direction of the relative longitudinal movement determines the winding direction (e.g., right-hand or left-hand). Step 504 can be accomplished using the motors 408, 442, 444.

In a third step 506, the relative distance between the unsecured portions 451, 453 of first strand 447 and the second strand 449 is changed, independent of the longitudinal displacement/motion of step 504. This can be achieved by movement of the first engagement arm 462 in relation to the second engagement arm 464, for example, by the fourth motor 468. Step 506 allows the first strand 447 to have a different pitch profile than the second strand 449, and thus provides a multifilar coil having the characteristics described in the present disclosure.

While embodiments have been shown and described, various modifications may be made without departing from the scope of the inventive concepts disclosed herein. The elongate shafts 200, 250 described herein may further incorporate braided portions, laser-cut hypo tube portions, or portions with a combination of any two or three of composite coil, braid, or laser cut hypo tube.

The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

What is claimed is:

1. A medical device comprising:
    an elongate shaft comprising:
        a multifilar coil comprising a first strand and a second strand wound in a same winding direction, the multifilar coil comprising a first section having a first end and a second end wherein all of the first strand between the first end and the second end of the first section defines a first pitch pattern, and all of the second strand between the first end and the second end of the first section defines a second pitch pattern, the second pitch pattern matching the first pitch pattern, the multifilar coil further comprising a second section having a first end and a second end, wherein all of the first strand between the first end and the second end of the second section defines a third pitch pattern, and all of the second strand between the first end and the second end of the second section defines a fourth pitch pattern, the third pitch pattern different from the fourth pitch pattern; and
    a first polymeric tubular member coextending within the multifilar coil, the first polymeric tubular member having a lumen extending therethrough and configured for placement of a guidewire.

2. The medical device of claim 1, wherein the multi-filar coil is a bifilar coil.

3. The medical device of claim 1, wherein the first and second strands in the first section of the multifilar coil are close-wound with a constant pitch pattern.

4. The medical device of claim 1, wherein the first section of the multifilar coil comprises a first sub-section and a second sub-section, the first strand and the second strand each having a first constant pitch along the first sub-section and the first strand and the second strand each having a variable pitch along the second sub-section.

5. The medical device of claim 4, wherein the variable pitch comprises a pitch that increases at a pitch increase rate having a constant value.

6. The medical device of claim 4, wherein the variable pitch comprises a pitch that increases at a pitch increase rate having a value that varies along a longitudinal axis of the multifilar coil.

7. The medical device of claim 4, wherein the multifilar coil further comprises a third section, the first strand and the second strand each having a second constant pitch in the third section, the second sub-section located between the first sub-section and the third section, the second constant pitch of the first strand and the second strand in the third section greater than the first constant pitch of the first strand and the second strand in the first sub-section.

8. The medical device of claim 7, wherein the third section is open-wound and the first sub-section is close-wound.

9. The medical device of claim 1, wherein the first strand and the second strand are longitudinally separated from each other between the first end and the second end of the second section of the multifilar coil, and wherein the first strand and the second strand are longitudinally close to each other between the first end and the second end of the first section of the multifilar coil.

10. The medical device of claim 1, wherein a first strand pitch increases at a first pitch increase rate between the first end and the second end of the second section of the multifilar coil, and a second strand pitch increases at a second pitch increase rate between the first end and the second end of the second section of the multifilar coil, the second pitch increase rate greater than the first pitch increase rate.

11. The medical device of claim 10, wherein the first pitch increase rate has a constant value.

12. The medical device of claim 11, wherein the second pitch increase rate has a constant value.

13. The medical device of claim 12, wherein the first pitch increase rate is between about 0.0002 inches per inch and about 0.050 inches per inch, and wherein the second pitch increase rate is between about 0.00025 inches per inch and about 0.060 inches per inch.

14. The medical device of claim 1, wherein the first strand and the second strand each comprise metallic round wire having a first wire diameter.

15. The medical device of claim 1, wherein the first section of the multifilar coil has a first outer diameter extending between its first end and second end, and wherein the second section of the multifilar coil has a second outer diameter extending between its first end and second, wherein the first outer diameter and the second outer diameter are substantially the same.

16. The medical device of claim 1, wherein the multifilar coil comprises a trifilar coil.

17. The medical device of claim 1, wherein the elongate shaft further comprises a second polymeric tubular member externally covering the multifilar coil.

18. The medical device of claim 1, wherein the multifilar coil is at least partially embedded within the first polymeric tubular member.

19. The medical device of claim 1, wherein at least one of the first strand or the second strand comprises a non-round wire having a maximum transverse dimension.

20. The medical device of claim 1, wherein the multifilar coil consists of strands comprising a high strength material.

21. The medical device of claim 20, wherein the high strength material comprises stainless steel.

22. The medical device of claim 20, wherein the strands comprising a high strength material comprise drawn filled tubes.

23. The medical device of claim 1, wherein the second section of the multifilar coil is intermediately located between the first section of the multifilar coil and a distal section of the multifilar coil.

* * * * *

UNITED STATES PATENT AND TRADEMARK OFFICE
CERTIFICATE OF CORRECTION

PATENT NO. : 10,512,753 B1
APPLICATION NO. : 16/213872
DATED : December 24, 2019
INVENTOR(S) : John Nguyen Page 1 of 1

It is certified that error appears in the above-identified patent and that said Letters Patent is hereby corrected as shown below:

In the Claims

Column 24, Claim 15, Line 11: insert -- end -- after "first end and second"

Signed and Sealed this
Seventeenth Day of March, 2020

Andrei Iancu
*Director of the United States Patent and Trademark Office*